United States Patent
Zhang et al.

(10) Patent No.: US 6,613,350 B1
(45) Date of Patent: *Sep. 2, 2003

(54) ELECTRICAL APPARATUS FOR HEATING TO A DESIRED TEMPERATURE FOR IMPROVED ADMINISTRATION OF PHARMACEUTICALLY ACTIVE COMPOUNDS

(75) Inventors: Jie Zhang, Salt Lake City, UT (US); Hao Zhang, Midvale, UT (US)

(73) Assignee: Zars, Inc., Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/544,897

(22) Filed: Apr. 7, 2000

Related U.S. Application Data

(62) Division of application No. 09/162,890, filed on Sep. 29, 1998, which is a continuation-in-part of application No. 08/819,880, filed on Mar. 18, 1997, now Pat. No. 5,919,479, which is a division of application No. 08/508,463, filed on Jul. 28, 1995, now Pat. No. 5,658,583.

(51) Int. Cl.$^7$ .......................... A61L 15/16; A61F 13/00; A61K 9/70

(52) U.S. Cl. ....................... 424/449; 424/402; 424/447; 424/448; 514/817; 514/937; 514/944; 602/41; 602/46

(58) Field of Search ................................ 724/449, 402, 724/447, 448; 524/817, 937, 944; 602/41, 46

(56) References Cited

U.S. PATENT DOCUMENTS

| | | | |
|---|---|---|---|
| 3,929,131 A | 12/1975 | Hardwick | 128/254 |
| 4,210,670 A | 7/1980 | Cooke | 424/324 |
| 4,230,105 A | 10/1980 | Harwood | 128/156 |

(List continued on next page.)

FOREIGN PATENT DOCUMENTS

| | | |
|---|---|---|
| GB | 2 163 956 A | 12/1988 |
| WO | 88/09169 | 1/1988 |
| WO | WO 97/01310 | 1/1997 |
| WO | WO 97/01311 | 1/1997 |
| WO | WO 97/01312 | 1/1997 |
| WO | WO 97/01313 | 1/1997 |
| WO | WO 97/36968 | 10/1997 |
| WO | WO 97/49361 | 12/1997 |
| WO | WO 98/28021 | 7/1998 |
| WO | WO 98/28024 | 7/1998 |
| WO | WO 98/29063 | 7/1998 |
| WO | WO 98/29064 | 7/1998 |
| WO | WO 98/29065 | 7/1998 |
| WO | WO 98/29066 | 7/1998 |
| WO | WO 98/29067 | 7/1998 |
| WO | WO 99/09917 | 3/1999 |
| WO | WO 99/09918 | 3/1999 |

OTHER PUBLICATIONS

Ghosh et al., Interpharm Press, Transdermal Topical Drug Delivery Syst., (1997) 327–355.*

Arky, et al., *Physicians' Desk Reference*, 1997, pp. 1336–1340.

Mack Publishing Company, "Stability of Pharmaceutical Products," *Pharmaceutical Sciences*, pp. 1481–1482, 1985.

McCafferty, et al., "Comparative In Vivo and In Vitro Assessment of the Percutaneous Absorption of Local Anaesthetics," *British Journal of Anaesthesia*, vol. 60, (1988), 64–69.

Woolfson, et al., "Concentration Response Analysis of Percutaneous Local Anaesthetic Formulations," *British Journal of Anaesthesia*, vol. 61, (1988), pp. 589–592.

McCafferty, et al., "In Vivo Assessment of Percutaneous Local Anaesthetic Preparations," *British Journal of Anaesthesia*, vol. 62, (1989), pp. 17–21.

Knutson et al., "Solvent–Mediated Alterations of the Stratum Corneum," *Journal of Controlled Release*, vol. 11, (1990), pp. 93–103.

Lycka, "EMLA, A New and Effective Topical Anesthetic," *J. Dermatol, Surg. Oncol.*, vol. 18, (1992), pp. 859–862.

McCafferty, et al., "New Patch Delivery System for Percutaneous Local Anaesthesia," *British Journal of Anaesthesia*, vol. 71, (1993) pp. 370–374.

Woolfson, *Percutaneous Local Anaesthesia*, E. Horwood, N.Y. (1993), pp. 166–170.

Astra USA, Inc., "EMLA Cream Product Information Form for American Hospital Formulary Service," (1993), pp. 1–28.

"Room Temperature," Macmillan, U.S.A., *Webster's New World College Dictionary*, Third Edition, 1997, p. 1165.

Florey, Klaus, *Analytical Profiles of Drug Substances*, vol. 15, 1986, pp. 150–231.

Florey, Klaus, *Analytical Profiles of Drug Substances*, vol. 12, 1983, pp. 73–105.

"Local Anesthetics, Parenteral, General Statement," *AHFS Drug Information*, 1992.

Florey, Klaus, *Analytical Profiles of Drug Substances*, vol. 18, 1989, pp. 379–411.

Sakamoto et al., "Dermal patch anesthesia: comparison of 10% lignocaine gel with absorption promoter and EMLA cream," *Anesthesia*, (1993), vol. 48, pp. 390–392.

(List continued on next page.)

Primary Examiner—Shelley A. Dodson
(74) Attorney, Agent, or Firm—Kirton & McConkie; Michael F. Krieger

(57) ABSTRACT

Methods and apparatus for improving administration of drugs through the use of heat and other physical means. The present invention relates to the use of heat and other physical means in conjunction with specially designed dermal drug delivery systems, conventional commercial dermal drug delivery systems, or drugs delivered into a sub-skin depot site via injection and other methods to alter, mainly increase, the drug release rate from the dermal drug delivery systems or the depot sites to accommodate certain clinical needs.

20 Claims, 14 Drawing Sheets

U.S. PATENT DOCUMENTS

| | | | |
|---|---|---|---|
| 4,286,592 A | 9/1981 | Chandrasekaran | 128/260 |
| 4,529,601 A | 7/1985 | Broberg | 514/626 |
| 4,685,911 A | 8/1987 | Konno et al. | 604/897 |
| 4,693,706 A | 9/1987 | Ennis, III | 604/87 |
| 4,747,841 A | 5/1988 | Kuratomi et al. | 604/291 |
| 4,830,855 A | 5/1989 | Stewart | 424/448 |
| 4,898,592 A | 2/1990 | Latzke et al. | 604/307 |
| 4,911,707 A | 3/1990 | Heiber et al. | 424/449 |
| 4,913,957 A | 4/1990 | Strack et al. | 424/286 |
| 4,963,360 A | 10/1990 | Argaud | 424/443 |
| 4,994,049 A | 2/1991 | Latzke et al. | 604/307 |
| 5,108,710 A | 4/1992 | Little et al. | 422/104 |
| 5,114,411 A | 5/1992 | Haber et al. | 604/203 |
| 5,128,137 A | 7/1992 | Muller et al. | 424/449 |
| 5,147,339 A | 9/1992 | Sundström | 604/307 |
| 5,213,129 A | 5/1993 | Someah et al. | 137/101.11 |
| 5,217,718 A | 6/1993 | Colley et al. | 424/449 |
| 5,229,133 A | 7/1993 | Wright et al. | 424/473 |
| 5,276,032 A | 1/1994 | King et al. | 514/239 |
| 5,279,594 A | 1/1994 | Jackson | 604/265 |
| 5,329,976 A | 7/1994 | Haber et al. | 141/25 |
| 5,330,452 A | 7/1994 | Zook | 604/307 |
| 5,364,350 A | 11/1994 | Dittman | 604/89 |
| 5,534,021 A | 7/1996 | Dvoretzky et al. | 607/112 |
| 5,580,573 A | 12/1996 | Kydonieus et al. | 424/449 |
| 5,605,536 A | 2/1997 | Sibalis | 604/20 |
| 5,626,571 A | 5/1997 | Young et al. | 604/370 |
| 5,651,768 A | 7/1997 | Sibalis | 604/20 |
| 5,658,583 A | 8/1997 | Zhang et al. | 424/402 |
| 5,662,624 A | 9/1997 | Sundstrom et al. | 604/291 |
| 5,728,057 A | 3/1998 | Ouellette et al. | 602/62 |
| 5,728,058 A | 3/1998 | Ouellette et al. | 602/62 |
| 5,728,146 A | 3/1998 | Burkett et al. | 607/109 |
| 5,733,255 A | 3/1998 | Dinh et al. | 604/20 |
| 5,735,889 A | 4/1998 | Burkett et al. | 607/96 |
| 5,741,318 A | 4/1998 | Ouellette et al. | 607/108 |
| 5,837,005 A | 11/1998 | Viltro et al. | 607/112 |
| D403,778 S | 1/1999 | Davis et al. | D24/206 |
| D403,779 S | 1/1999 | Davis et al. | D24/206 |
| 5,860,945 A | 1/1999 | Cramer et al. | 602/62 |
| D407,822 S | 4/1999 | Davis et al. | D24/206 |
| D407,824 S | 4/1999 | Davis et al. | D24/206 |
| D408,923 S | 4/1999 | Davis et al. | D24/206 |
| D409,757 S | 5/1999 | Davis et al. | D24/206 |
| 5,904,710 A | 5/1999 | Davis et al. | 607/108 |
| 5,906,637 A | 5/1999 | Davis et al. | 607/108 |
| 5,906,830 A | 5/1999 | Farinas et al. | 424/448 |
| 5,919,479 A | 7/1999 | Zhang et al. | 424/449 |
| 5,925,072 A | 7/1999 | Cramer et al. | 607/108 |
| D412,751 S | 8/1999 | Davis et al. | D24/206 |
| D417,283 S | 11/1999 | Davis et al. | D24/206 |
| 5,980,562 A | 11/1999 | Ouellette et al. | 607/108 |
| 5,984,995 A | 11/1999 | White | 75/230 |
| D418,606 S | 1/2000 | Davis et al. | D24/206 |
| 6,019,782 A | 2/2000 | Davis et al. | 607/96 |
| 6,020,040 A | 2/2000 | Cramer et al. | 428/64.1 |
| 6,024,761 A | 2/2000 | Barone et al. | 607/108 |
| 6,042,673 A | 3/2000 | Johnson et al. | 156/227 |
| 6,048,326 A | 4/2000 | Davis et al. | 602/26 |

OTHER PUBLICATIONS

Dvoretzky, Israel, M.D., Hyperthermia Therapy for Warts Utilizing a Self–administered Exothermic Patch, *Dermal Surgery*, (1996), vol. 22, pp. 1035–1039.

Stern, Peter, M.D. and Levine, Norman, M.D., "Controlled Localized Heat Therapy in Cutaneous Warts," *Arch. Dermatol*, (Jul. 1992), vol. 128, pp. 945–948.

* cited by examiner

ELECTRICAL APPARATUS FOR HEATING TO A DESIRED TEMPERATURE FOR IMPROVED ADMINISTRATION OF PHARMACEUTICALLY ACTIVE COMPOUNDS

The present application is a divisional of U.S. application Ser. No. 09/162,890 filed Sep. 29, 1998, which is a continuation-in-part of U.S. application Ser. No. 08/819,880, filed Mar. 18, 1997, now U.S. Pat. No. 5,919,479, which is a divisional of U.S. application Ser. No. 08/508,463, filed Jul. 28, 1995, now U.S. Pat. No. 5,658,583, hereby incorporated herein by reference.

BACKGROUND OF THE INVENTION

Related Applications: The present application is a continuation-in-part of U.S. application Ser. No. 08/819,880, filed Mar. 18, 1997 now U.S. Pat. No. 5,919470 which is a division of U.S. application Ser. No. 08/508,463, filed Jul. 28, 1995, now U.S. Pat. No. 5,658,583, hereby incorporated herein by reference.

1. Field of the Invention

The present invention relates to methods and apparatus for administration of drugs. More particularly, the present invention relates to using controlled heat and other physical means to improve dermal, mucosal, and injection administration of drugs.

2. State of the Art

The dermal administration of pharmaceutically active compounds involves the direct application of a pharmaceutically active formulation(s) to the skin, wherein the skin absorbs a portion of the pharmaceutically active compound which is then taken up by the blood stream. Such administration has long been known in the practice of medicine and continues to be an important technique in the delivery of pharmaceutically active compounds. For example, U.S. Pat. No. 4,286,592 issued Sep. 1, 1981 to Chandrasekaran shows a bandage for administering drugs to a user's skin consisting of an impermeable backing layer, a drug reservoir layer composed of a drug and a carrier, and a contact adhesive layer by which the bandage is affixed to the skin.

Such dermal administration offers many important advantages over other delivery techniques, such as injection, oral tablets and capsules. These advantages include being non-invasive (thus, less risk of infection), avoiding first pass metabolism (metabolism of the drug in the liver when the drug is taken orally and absorbed through the gastrointestinal tract), and avoiding of high peaks and low valleys of concentration of pharmaceutically active compounds in a patient's bloodstream. In particular, high peaks and low valleys of concentration are typical in injection and oral administrations and are often associated with undesirable side effects and/or less than satisfactory intended effects.

The term "dermal drug delivery system" or "DDDS", as used herein, is defined as an article or apparatus containing pharmaceutically active compound(s) for delivery into the skin, the regional tissues under the skin, the systemic circulation, or other targeting site(s) in a human body via skin permeation. The term "DDDS" in this application, unless otherwise specified, only refer to those systems in which the main driving force for drug permeation is the drug concentration gradient.

The term "skin", as used herein, is defined to include stratum corneum covered skin and mucosal membranes.

The term "drug", as used herein, is defined to include any pharmaceutically active compound including but not limited to compounds that treat diseases, injuries, undesirable symptoms, and improve or maintain health.

The terms "targeted area" or "targeted areas", as used herein, are defined to include a systemic bloodstream of a human body, areas of a human body which can be reached by a systemic bloodstream including, but not limited to muscles, brain, liver, kidneys, etc., and body tissue regions proximate a location of an administered drug.

In DDDSs, a drug(s) is usually contained in a formulation, such as a hydro-alcohol gel, and may include a rate limiting membrane between the formulation and skin for minimizing the variation in the permeation of the drug. When a DDDS is applied to skin, the drug begins to transport out of the formulation, and transport across the rate limiting membrane (if present). The drug then enters the skin, enters blood vessels and tissues under the skin, and is taken into the systemic circulation of the body by the blood. At least some DDDSs have certain amount of pharmaceutically active compound in or on the skin side of the rate limiting membrane (if present) prior to use. In those DDDSs, that portion of the drug on the skin side of the rate limiting membrane will enter the skin without passing through the rate limiting membrane. For many drugs, a significant portion of the dermally absorbed drug is stored in the skin and/or tissues under the skin (hereinafter referred as "depot sites") before being gradually taken into the systemic circulation (hereinafter referred as "depot effect"). This depot effect is believed to be at least partially responsible for the delayed appearance of the drug in the systemic circulation after the application of some DDDSs and for continued delivery of the drug into the systemic circulation after the removal of some DDDSs from the skin.

After placing a DDDS on the skin, the drug concentration in the blood typically remains at or near zero for a period of time, before starting to gradually increase and reach a concentration deemed to be medicinally beneficial, called the "therapeutic level" (the time it takes to reach the therapeutic level is referred to hereinafter as the "onset time"). Ideally, the concentration of the drug in the bloodstream should plateau (i.e., reach a substantially steady state) at a level slightly higher than the therapeutic level and should remain there for extended period of time. For a given person and a given DDDS, the "concentration of the drug in the bloodstream vs. time" relationship usually cannot be altered under normal application conditions.

The onset time and the delivery rate of the drug into the targeted area(s) of the body for a typical DDDS are usually determined by several factors, including: the rate of release of the drug from the formulation, the permeability of the drug across the rate limiting membrane (if a rate limiting membrane is utilized), the permeability of the drug across the skin (especially the stratum corneum layer), drug storage in and release from the depot sites, the permeability of the walls of the blood vessels, and the circulation of blood and other body fluid in the tissues (including the skin) under and around the DDDS. Although these primary factors affecting onset time and delivery rate are known, no existing DDDS is designed to have alterable delivery rate in the course of the application of the drug.

While a DDDS works well in many aspects, current dermal drug delivery technology has some serious limitations, including: 1) the onset time being undesirably long for many DDDSs; 2) the rate that the drug is taken into the systemic circulation or the targeted area(s) of the body cannot be easily varied once the DDDS is applied onto the skin and, when the steady state delivery rate is achieved, it cannot be easily changed; and 3) the skin permeability being so low that many drugs are excluded from dermal delivery because the amount of drug delivered is not high enough to reach a therapeutic level. In addition, temperature variations in the skin and the DDDS are believed contribute to the variation of dermal absorption of drugs.

It is known that elevated temperature can increase the absorption of drugs through the skin. U.S. Pat. No. 4,898, 592, issued Feb. 6, 1990 to Latzke et al., relates to a device for the application of heated transdermally absorbable active substances which includes a carrier impregnated with a transdermally absorbable active substance and a support. The support is a laminate made up of one or more polymeric layers and optionally includes a heat conductive element. This heat conductive element is used for distribution of the patient's body heat such that absorption of the active substance is enhanced. U.S. Pat. No. 4,230,105, issued Oct. 28, 1980 to Harwood, discloses a bandage with a drug and a heat-generating substance, preferably intermixed, to enhance the rate of absorption of the drug by a user's skin. Separate drug and heat-generating substance layers are also disclosed. U.S. Pat. No. 4,685,911, issued Aug. 11, 1987 to Konno et al., discloses a skin patch including a drug component, and an optional heating element for melting the drug-containing formulation if body temperature is inadequate to do so.

Another area of administration involves delivering drugs in controlled/extended release form/formulations ("form/formulation") into the skin or tissues under the skin (the residing place for these form/formulations are hereinafter referred as "storage sites") which results in the drugs being released from the storage sites in a controlled/extended fashion. The most common technique to deliver the form/formulations into the storage sites is by injection. Other techniques may also be used, such as implantation and forcing the form/formulation into the skin with high-speed hitting. However, once the form/formulation is delivered into the storage sites, it is usually difficult to alter the rate, known as the "release rate", that the drug is released from the form/formulation at the storage sites, and taken into the systemic circulation or the targeted area(s) of the body.

Yet another area of administration involves injecting drugs subcutaneously or intramuscularly. In some clinical situations, it is beneficial to accelerate the speed of drug absorption into the systemic circulation or other targeted areas(s) in the body after such injection.

Therefore, it would be advantageous to develop methods and apparatus to improve the drug administration of DDDSs, and, more specifically, to make the use of DDDSs more flexible, controllable, and titratable (varying the drug delivery rate, amount, or period according to the biological effect of the drug) to better accommodate various clinical needs. It would also be advantageous to develop methods and apparatus to make dermal delivery possible for drugs which are currently excluded because of low skin permeability. It would further be advantageous to develop means to alter mainly to increase the drug absorption rate from the storage sites or injection sites in such ways that can accommodate certain clinical needs.

SUMMARY OF THE INVENTION

The present invention relates to various methods and apparatus for improved dermal and mucosal administration of drugs through the use of controlled heat and other physical means. The present invention further relates to methods and apparatus for using controlled heat and other physical means to alter, mainly increase, the drug release rate from the storage sites or injection sites in such ways to accommodate certain clinical needs.

In the application of a DDDS, the absorption of the drug is usually determined by a number of factors including: the diffusion coefficient of drug molecules in the drug formulation, the permeability coefficient of the drug across the rate limiting membrane (if one is used in the DDDS), the concentration of dissolved drug in the formulation, the skin permeability of the drug, drug storage in and release from the depot sites, the body fluid (including blood) circulation in the skin and/or other tissues under the skin, and permeability of the walls of capillary blood vessels in the sub-skin tissues. Thus, in order to address the limitations of the current dermal drug delivery technologies, it is desirable to have control over and have the capability to alter these drug absorption factors. It is believed that controlled heating/cooling can potentially affect each one of the above factors.

Specifically, increased temperature generally can increase diffusion coefficients of the drugs in the formulations and their permeability across the rate limiting membrane and skin. Increased heat also increases the blood and/or other body fluid flow in the tissues under the DDDS, which should carry the drug molecules into the systemic circulation at faster rates. Additionally, increased temperature also increases the permeability of the walls of the capillary blood vessels in the sub-skin tissues. Furthermore, increased temperature can increase the solubility of most, if not all, drugs in their formulations which, in formulations with undissolved drugs, should increase permeation driving force. Of course, cooling should have substantially the opposite effect. Thus, the present invention uses controlled heating/cooling to affect each of the above factors for obtaining controllable dermal absorption of drugs.

The present invention also uses controlled heating/cooling in several novel ways to make dermal drug delivery more flexible and more controllable in order to deal with various clinical conditions and to meet the needs of individual patients. More broadly, this invention provides novel methods and apparatus for controlled heating/cooling (hereinafter "temperature control apparatus") during the application of the DDDS, such that heating can be initiated, reduced, increased, and stopped to accommodate the needs.

Another embodiment of the present invention is to determine the duration of controlled heating on DDDS based on the effect of the drug for obtaining adequate amount of the extra drug and minimizing under-treatment and side effects associated with under and over dosing.

Through the proper selection, based on the specific application and/or the individual patient's need, of the moment(s) to initiate controlled heating, heating temperature, and moment(s) to stop the controlled heating, the following control/manipulation of the absorption rates should be achieved: 1) shorten the onset time of the drug in the DDDS without significantly changing its steady state delivery rates; 2) provide proper amount of extra drug during the application of a DDDS when needed; and 3) increase the drug absorption rate throughout a significant period of duration or throughout the entire duration of the DDDS application.

Shortening of onset time is important in situations where the DDDS provides adequate steady state deliver rates, but the onset is too slow. Providing the proper amount of extra drug is important where a DDDS delivers adequate "baseline" amount of the drug, but the patient needs extra drug at particular moment(s) for particular period(s) of time during the application of the DDDS. Increasing the drug absorption rate is used for the patients who need higher drug delivery rates from the DDDS.

The first of above approach can be achieved by applying controlled heating at the starting time of the DDDS application, and design the heating to last long enough to cause the concentration of the drug in the systemic circulation or other targeted area of the body to rise toward the therapeutic levels, and stops (may be gradually) shortly after that. The second approach may be achieved by applying controlled heat when a need to obtain extra drug are rises, and terminating the controlled heating either at a predetermined moment or when the desired effect of the extra drug is achieved. The third approach can be achieved by applying the controlled heat at the starting time of the DDDS application. In all those three approaches, temperature of the controlled heating needs to be designed to control the degree of increase in said that drug delivery rates.

Such embodiments are particularly useful in situations where the user of a DDDS gets adequate drug absorption most of the time, but there are periods of time in which increased or decreased drug absorption is desirable. For example, during the treatment of cancer patients with an analgesic, such as with Duragesic® dermal fentanyl patches (distributed by Janssen Pharmaceutica, Inc. of Piscataway, N.J., USA), "breakthrough" pain (a suddenly increased and relatively short lasting pain, in addition to a continuous "baseline" pain) may occur. An additional analgesic dose, in the form of a tablet, an oral or nasal mucosal absorption dosage form, or an injection needs to be given to treat the breakthrough pain. But with the help of controlled heat, one single DDDS may take care of both baseline pain and episodes of breakthrough pain. With the help of controlled heat, a heating patch can be placed on top of the Duragesic® patch when an episode of breakthrough pain occurs to deliver more fentanyl into the systemic circulation. The heating duration of the heating patch is preferably designed to be long enough to deliver sufficient extra fentanyl, but not long enough to deliver the extra amount of fentanyl that may pose a risk to the patient. The patient may also remove the heating patch when the breakthrough pain begins to diminish. Thus, with the help of controlled heat, one single Duragesic® dermal fentanyl patch may take care of both baseline pain and episodes of breakthrough pain. For another example, a dermal nicotine patch user may obtain extra nicotine for a suddenly increased nicotine craving by heating the nicotine patch.

Due to low skin permeability of the skin, onset times of conventional DDDSs are usually quite long, and often undesirably long. Thus, another aspect of the present invention is to provide methods and apparatus for using controlled heat to shorten the onset times of DDDSs, preferably without substantially changing the steady state drug delivery rates. A particularly useful application of this aspect of the present invention is to provide a controlled heating apparatus for use with conventional, commercially available DDDSs to shorten the onset times in clinical use, without having to re-design the DDDSs or adjust their steady state drug delivery rates.

It is believed that an important cause for variation in drug absorption in DDDSs is variation in temperature of the DDDSs and the adjacent skin caused by variations in ambient temperature and/or physical condition of the person. This temperature variation can, of course, potentially affect all of the factors that collectively determine the ultimate drug delivery rates of the DDDSs. Thus, the present invention of providing methods and apparatus to use controlled heating/cooling also minimizes the variation in temperature of the skin and the DDDSs applied on the skin. It is also contemplated that an insulating material can be incorporated with the controlled temperature apparatus to assist in not only minimizing the temperature variation, but also increasing the temperature of the DDDS and the skin under it (by decreasing heat loss), each of which tend to increase dermal drug absorption.

The present invention also relates to methods and apparatus for using an insulating device, such as a cover made of insulating material (such as closed-cell foam tape) with adhesive edges, and a size slightly larger than the DDDS or the area over an injected drug, to cover the DDDS/injected drug when the DDDS and/or the skin of the user is exposed to extreme temperature (such as a hot shower or bath, direct sunlight, etc.).

An important area in modem anesthesiology is patient controlled analgesia (hereinafter "PCA"), in which the patient gives himself a dose of analgesic when he feels the need. The ranges of the dose and dosing frequency are usually set by a care giver (i.e., caring physician, nurse, etc.). In many PCA situations, the patient receives a baseline rate of analgesic, and gets extra bolus analgesic when he feels that it is needed. The technology in the present invention may be used for a PCA in which the patient gets the baseline dose by a regular dermal analgesic patch and the extra ("rescue") dose by heating the dermal analgesic patch. The heating temperature and duration needs to be designed to deliver a proper amount of extra dose.

Drugs in controlled or extended release forms or formulations may be delivered into depot/storage sites in the skin and/or the tissues under the skin with methods such as injection, implantation, hitting the drug/drug formulation on the skin with supersonic speed, and embedding the drug/drug formulation onto the skin. The controlled/extended form/formulation allows the drug to be released gradually into the surrounding tissues and/or systemic circulation over an extended period of time. For instance, extended release insulin (such as Ultralente® zinc insulin—Eli Lilly and Co.) can be injected subcutaneously to deliver insulin into the patient's systemic circulation over an extended period of time. However, once the drug in the controlled/extended form/formulation is delivered to the storage sites, it is usually difficult to alter or control the course of drug release. The apparatus and methods of the present invention allow controlled heat to increase and controlled cooling to decrease, the drug release from the controlled/extended form/formulation after it is delivered into the depot/storage sites. For example, many diabetic patients need additional insulin shortly before meals to suppress the blood sugar increase resulting from the meals. However, the release rate of the subcutaneously injected extended release insulin is relatively constant. With the methods and apparatus in the invention, a diabetic patient may inject a subcutaneous extended release insulin in the morning and apply controlled heat on the skin of the injection site for a duration of time shortly before ingestion of a meal to obtain additional insulin to suppress the sugar from the meal. The controlled heat increases the flow of blood and other body fluid surrounding the storage sites and is believed to increase the dissolution rate of insulin. It is, of course, understood that whether a given controlled/extended release formulation in the depot/storage sites can actually release extra drug with increased temperature depends on the nature of the drug form/formulation. However, since heat is known or expected to increase the diffusion speed of drugs in their formulations, increase the permeability of blood vessel walls, and increases the circulation of body fluid surrounding the depot sites, each of which tend to favor increased drug release, the heat-induced extra drug release is expected to take place for many, if not most, controlled/extended drug form/formulation delivered into sub-skin storage sites.

One important aspect of the present invention is to properly choose the temperature of the controlled heat and the moment(s) to initiate and stop the controlled heat in the applications with injected drug formulations, especially extended/controlled release formulations, to accommodate the needs of different therapies and individual patients, in ways similar to the applications with DDDSs discussed above.

Many biodegradable polymers may be used to make controlled/extended release formulations. Of particular note are the biogradable lactic/glycolic acid polymers described in Chapters 29 and 33 of *Encyclopedic Handbook of Biomaterials and Bioengineering*, edited by Donald L. Wise, et al., publ. Marcel Dekker, 1995, hereby incorporated herein by reference. It is one important aspect of the present invention to use controlled heat, as discussed above, to control/regulate drug release rates from controlled/extended release formulations made with such polymers, and preferably, prepared using the methods described in the *Encyclopedic Handbook of Biomaterials and Bioengineering*.

For drugs where quick systemic absorption is important, the present invention may be beneficial. For example, it is generally agreed that to successfully treat a migraine headache, concentrations of an anti-migraine drug, such as dihydroergotamine, in the bloodstream must reach a therapeutic level within a certain time from the onset of migraine headache. In such situations, the heating devices, as discussed above, may be used with normal injection of drugs. Since heat can usually increase the diffusion speed of drugs in their formulations, increase the permeability of blood vessel walls, and increases the circulation of body fluid surrounding the injection site, the drug will enter the system circulation more quickly.

One of the more important aspects of the present invention is the apparatus for generating and providing controlled heating. These controlled heat generating apparatus generally comprise a heat generating portion and a means to pass the heat generated by the heat generating portion to the DDDSs, the skin, and/or the sub-skin depot and storage sites. These controlled heat generating apparatus generally further include a mechanism (such as tape, adhesive, and the like) for affixing apparatus onto the DDDSs and/or the skin. Preferably, the affixation mechanism securely holds the controlled heat generating apparatus in place while in use, but it also allows relatively easy removal after use. Additionally, these controlled heat generating apparatus may further include a mechanism for terminating the generation of heat. The shape and size of the bottom of the controlled heat generating apparatus are generally specially made to accommodate the DDDSs with which they are to be employed.

One embodiment of a controlled heat generating apparatus is a shallow chamber including non-air permeable side wall(s), a bottom wall, and a non-air permeable top wall which has area(s) with limited and desired air permeability (e.g., holes covered with a microporous membrane). A heat generating medium is disposed within the shallow chamber. The heat generating medium preferably comprises a mixture of iron powder, activated carbon, salt, water, and, optionally, sawdust. The controlled heat generating apparatus is preferably stored in an air-tight container from which it is removed prior to use. After removal from the air-tight container, oxygen in the atmosphere ("ambient oxygen") flows into heat generating medium through the areas on the non-air permeable top with desired air-permeability to initiate a heat generating oxidation reaction (i.e., an exothermic reaction). The desired heating temperature and duration can be obtained by selecting the air exposure of the top (e.g., selecting the right size and number of holes on the cover and/or selecting the microporous membrane covering the holes for a specific air permeability), and/or by selecting the right quantities and/or ratios of components of the heat generating medium.

This embodiment of the controlled heat generating apparatus preferably includes a mechanism for affixing the controlled heat generating apparatus onto the skin or a DDDS that is applied to the skin. For applications where the removal or termination of the heating might be necessary, the heat generating apparatus may also have a mechanism for allowing easy removal from the DDDS and/or the skin or for termination of the heating. One mechanism for allowing easy removal of the shallow chamber from a DDDS without removing the latter from the skin comprises a layer of adhesive on the side walls of the heat generating apparatus with an non-adhesive area or less adhesive area (less adhesive than the adhesive affixing the DDDS to the skin) at the bottom of the shallow chamber, with the non- or less adhesive area having a shape similar to that of the DDDS. When such a heat generating apparatus is applied onto the DDDS which is on the skin, the adhesive at the bottom of the side walls of the heat generating apparatus adheres to the skin, and non- or less adhesive part is on top of, but not adhered or not strongly adhered to, the DDDS. This allows for removal of the heat generating apparatus without disturbing the DDDS.

Although one application of such a heat generating apparatus is to be used in conjunction with a DDDS, it is understood that the heat generating apparatus can also be applied directly to the skin to increase the release of drugs from depot sites or sites of injection or implantation of controlled released drugs (storage sites), or to accelerate the absorption of subcutaneously or intramuscularly injected drugs.

The heat generating mechanism of the present invention for the controlled heat generating apparatus is not limited to the preferred exothermic reaction mixture of iron powder, activated carbon, salt, water, and, optionally, sawdust, but may include a heating unit whose heat is generated by electricity. The electric heating unit, preferably, includes a two dimensional surface to pass the heat to the DDDS and/or the skin. The electric heating unit may also include a temperature feedback system and a temperature sensor that can be placed on the DDDS or the skin. The temperature sensor monitors the temperature at the DDDS or skin and transmits an electric signal based on the sensed temperature to a controller which regulates the electric current or voltage to the electric heating unit to keep the temperature at the DDDS or skin at desired levels. Preferably, a double sided adhesive tape can be used to affix the electric heating unit onto the skin.

The heat generating mechanism may also comprise an infrared generating unit and a mechanism to direct the infrared radiation onto the DDDS or the skin. It may also have a temperature feedback system and a temperature sensor that can be placed on the DDDS or the skin to control the intensity of the infrared emission to maintain the temperature at the DDDS or skin at desired levels.

The heat generating mechanism may further comprise a microwave generation unit and a mechanism to direct the microwave radiation onto the DDDS or the skin. Again, the heat generating mechanism may have a temperature feedback system and a temperature sensor to regulate the intensity of the microwave emission to maintain the temperature at the DDDS or skin at desired levels.

The heat generating mechanism may yet further comprise a container containing supercooled liquid which generates heat from crystallization ("exothermic"). The crystallization is initiated within the container, such as by bending a metal piece in the supercooled liquid, and the container is placed on a DDDS or on the skin. The heat which is released from the crystallization process is passed to the DDDS and/or the skin. However, heat generated by crystallization usually does not maintain a constant level over extended time. Thus, such a heat generating mechanism is not ideal for applications where elevated temperature in a narrow range over an extended time is necessary, but is useful where only a short heating duration is needed, such as with a DDDS that would benefit from short heating duration to minimize the onset time.

Although, in general, most benefits for DDDSs are realized from increased drug absorption and release rates by heating, there are circumstances where it may be desirable to be able to both increase and decrease the drug absorption and release rates. It is understood that for a more complete control in dermal and controlled/extended release drug administration that a mechanism for providing both heating or cooling, depending on need, would be advantageous. Thus, a novel approach of this invention is to provide methods and apparatus for providing heating or cooling to the DDDSs, the skin and/or the tissues under it, or the controlled/extended release drug form/formulation in the skin or the tissues under the skin, such that the drug absorption and/or release can be controlled. The heating/cooling mechanism comprises a thermoelectric module which functions as a heat pump wherein the power supply may be reversed depending on whether heating or cooling is desired. A cooling mechanism can include an endothermic crystallization mechanism similar to the exothermic crystallization mechanism discussed above.

It is, of course, understood that the use of controlled heating and/or cooling to control drug absorption and/or release are equally applicable to controlled/extended form/formulations after they are delivered into the skin and/or tissues under the skin. However, physical mechanisms other than heating and/or cooling may also be used for the same purpose. Thus, it is novel approach of this invention to provide methods and apparatus to use ultrasound, electric current, and mechanical vibration to induce extra drug release from controlled/extended release form/formulations which are already delivered into the body and that are responsive to these physical induction means.

BRIEF DESCRIPTION OF THE DRAWINGS

While the specification concludes with claims particularly pointing out and distinctly claiming that which is regarded as the present invention, the objects and advantages of this invention may be more readily ascertained from the following description of the invention, when read in conjunction with the accompanying drawings in which:

DETAILED DESCRIPTION OF THE ILLUSTRATED EMBODIMENT

FIGS. 1–32 illustrate various views of temperature control or other apparatuses and dermal drug delivery systems. It should be understood that the figures presented in conjunction with this description are not meant to be illustrative of actual views of any particular apparatus, but are merely idealized representations which are employed to more clearly and fully depict the present invention than would otherwise be possible. Elements common between the figures retain the same numeric designations.

Figure 1:
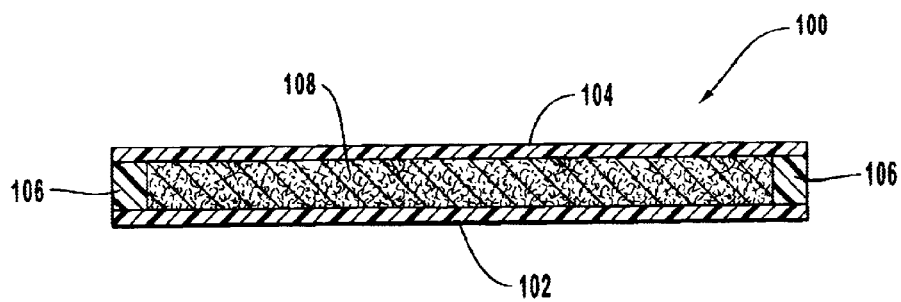
FIG. 1 is a side cross-sectional view of an embodiment of a temperature control apparatus according to the present invention.

FIG. 1 illustrates a temperature control apparatus 100 of the present invention comprising a chamber defined by a bottom wall 102, a top wall 104, and side walls 106 wherein a temperature regulating mechanism 108 is disposed within the chamber. The temperature regulating mechanism 108 can include a heat generating oxidation reaction mechanism, electric heating unit, exothermic crystallization mechanism, endothermic crystallization mechanism, heating/cooling mechanism, cooling mechanism, or the like.

Figure 2:
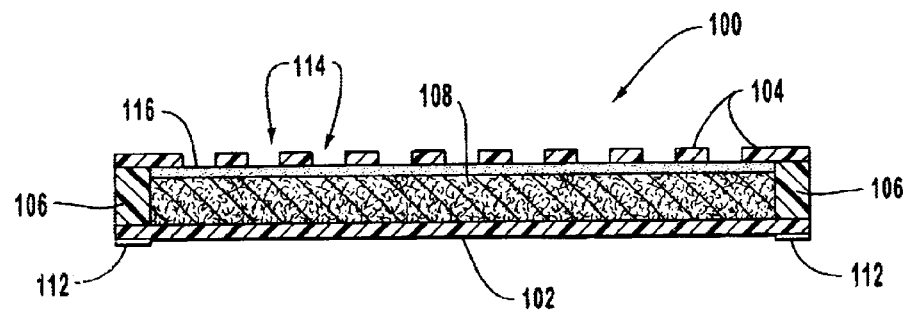
FIG. 2 is a side cross-sectional view of another embodiment of a temperature control apparatus according to the present invention.

FIG. 2 illustrates a temperature control apparatus 100 comprising a temperature regulating mechanism 108 surrounded by a bottom wall 102, a top wall 104, and side walls 106. The bottom wall 102 is preferably a plastic material and the side walls 106 are preferably made of a flexible non-air permeable material, such as non-air permeable closed-cell foam material. A portion or all of the bottom wall 102 of the temperature control apparatus 100 includes an adhesive material 112 for attachment to a DDDS or to the skin of a patient. The temperature regulating mechanism 108 preferably comprises a composition of activated carbon, iron powder, sodium chloride and water in a proper ratio. Optionally, saw dust may be added to the composition to facilitate the airflow within the composition and/or provide "body" to the composition. The top wall 104 is preferably also a flexible non-air permeable material having holes 114 therethrough. An air permeable membrane 116 is, preferably, disposed between the top wall 104 and the temperature regulating mechanism 108 to regulate the amount of air reaching the temperature regulating mechanism 108 through the holes 114. The air permeable membrane 116 is preferably a porous film (such as No. 9711 microporous polyethylene film—CoTran™, 3M Corporation, Minneapolis, Minn., USA).

Figure 3:
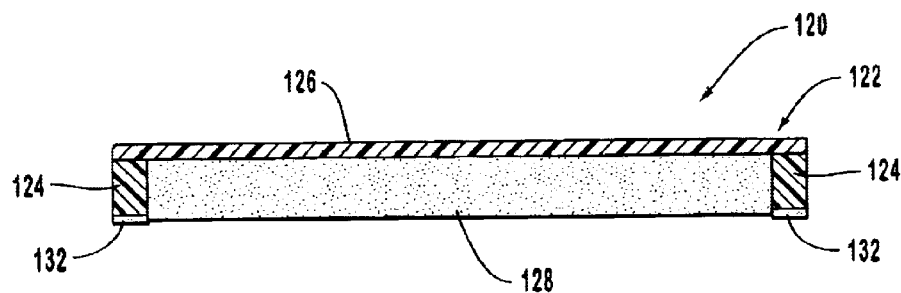
FIG. 3 is a side cross-sectional view of an embodiment of a dermal drug delivery system according to the present invention.

FIG. 3 illustrates a dermal drug delivery system 120 (hereinafter "DDDS 120") comprising a housing 122 made of a flexible material(s). The housing 122 preferably comprises side walls 124 and a top wall 126 with a drug formulation 128 disposed within the housing 122. Preferably, the bottom of the DDDS side walls 124 include an adhesive 132 to affix the DDDS 120 to the skin of a patient.

Figure 4:
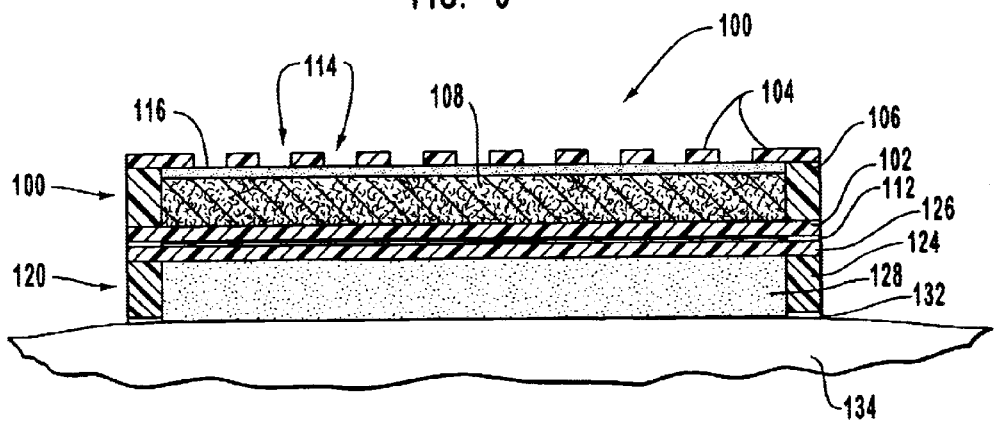
FIG. 4 is a side cross-sectional view of the temperature control apparatus of FIG. 2 in conjunction with the dermal drug delivery system of FIG. 3 according to the present invention.

FIG. 4 illustrates the temperature control apparatus 100 of FIG. 2 attached to the DDDS 120 of FIG. 3. The DDDS 120 attached to a portion of the skin 134 of a patient. The area of the temperature regulating mechanism 108 is preferably slightly larger than that of the drug formulation 128. The temperature control apparatus 100 and the DDDS 120 are preferably stored in separated compartments of an air tight container (or in separate air tight containers).

EXAMPLE 1

One example of using the embodiment of the present invention illustrated in FIGS. 2–4 for administering analgesic material for relief of pain consists of a patient or care giver placing the DDDS 120 on the skin 134 of the patient, which preferably adheres to the skin 134 with DDDS adhesive 132. The patient or care giver then attaches the temperature control apparatus 100 on top of the DDDS 120, which adheres to the DDDS 120 with temperature control apparatus adhesive 112. Oxygen in ambient air flows into the temperature regulating mechanism 108 through holes 114 and air permeable membrane 116. Of course, it is understood that the rate at which oxygen contacts the temperature regulating mechanism 108 is determined by the size and number of the holes 114 on the top wall 104, as well as the air permeability of the air permeable membrane 116. A heat generating (exothermic) chemical reaction occurs in the temperature regulating mechanism 108. Heat from this reaction passes through the temperature control apparatus bottom wall 102, through the DDDS top wall 126, through the drug formulation 128, and increases the temperature of the patient's skin 134 under the DDDS 120.

In actual experimentation, the temperature control apparatus 100 comprised the side walls 106 defined by a ⅛ inch thick rectangular foam tape (2 layers of No.1779 ¹⁄₁₆" white foam tape, 3M Corporation, Minneapolis, Minn., USA) with an outer dimension of about 2.25 inches by 4 inches with an opening therein having an inner dimension of about 1.75 inches by 3.5 inches, the bottom wall 102 comprising rectangular medical tape (No. 1525L plastic medical tape, 3M Corporation, Minneapolis, Minn., USA) of a dimension of about 2.25 inches by 4 inches with a non-adhesive side attached to the bottom of the side walls 106, and a top wall 104 comprising a rectangular ¹⁄₃₂ inch thick foam tape (No. 9773 ¹⁄₃₂" tan foam tape, 3M Corporation, Minneapolis, Minnesota, USA) with forty-five holes 114 (diameters approximately 0.9 mm, in a 5 by 9 pattern with about 7.5 mm to 8.0 mm center spacing) therethrough. The side walls 106, the bottom wall 102, and the top wall 104 defined a chamber. The holes 114 of the top wall 104 were covered by an air permeable membrane 116 comprising a porous membrane (No. 9711 microporous polyethylene film— CoTran™, 3M Corporation, Minneapolis, Minn., USA) disposed between the top wall 104 and the temperature regulating mechanism 108. The side walls 106, the bottom wall 102, and the top wall 104 all had ⅛" rounded corners. The temperature regulating mechanism 108 disposed in the chamber comprised a mixture of activated carbon (HDC grade—Norit Americas, Inc., USA), iron powder (grade R1430—ISP Technologies, USA), saw dust (Wood Flour, Pine—Pioneer Sawdust, USA), sodium chloride and water in the weight ratio of approximately 5:16:3:2:6 weighing approximately 16.5 grams. The temperature control apparatus 100 was sealed in an air-tight container immediately after fabrication.

Figure 5:
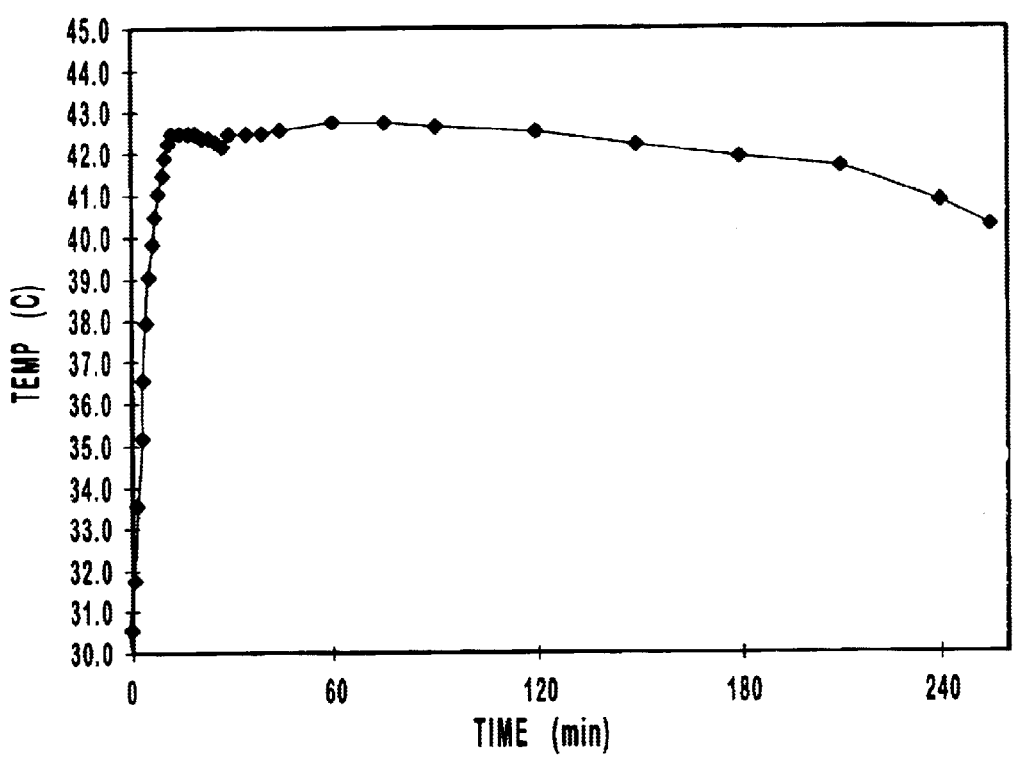
FIG. 5 is a graph of time versus temperature for a temperature control apparatus according to the present invention.

The temperature control apparatus 100 was tested on a volunteer with a temperature probe placed between the temperature control apparatus 100 and the volunteer's skin to measure the temperature. The results of this temperature experiment is illustrated in FIG. 5 and Table A, which shows that the temperature control apparatus 100 is capable of keeping the skin temperature to a narrow, elevated range of about 41° C. to 43° C. for extended period of time (at least about 240 minutes).

TABLE A

| Time (minutes) | Temperature (° C.) |
| --- | --- |
| 0 | 30.6 |
| 1 | 31.8 |
| 2 | 33.6 |
| 3 | 35.2 |
| 4 | 36.6 |
| 5 | 38.0 |
| 6 | 39.1 |
| 7 | 39.9 |
| 8 | 40.5 |
| 9 | 41.1 |
| 10 | 41.5 |
| 11 | 41.9 |
| 12 | 42.3 |
| 13 | 42.5 |
| 14 | 42.5 |
| 15 | 42.5 |
| 16 | 42.5 |
| 17 | 42.5 |
| 18 | 42.5 |
| 19 | 42.5 |
| 20 | 42.5 |
| 22 | 42.4 |
| 24 | 42.4 |
| 26 | 42.3 |
| 28 | 42.2 |
| 30 | 42.5 |
| 35 | 42.5 |
| 40 | 42.6 |
| 45 | 42.6 |
| 60 | 42.5 |
| 75 | 42.8 |
| 90 | 42.7 |
| 120 | 42.6 |
| 150 | 42.3 |
| 180 | 42.0 |
| 210 | 41.8 |
| 240 | 41.0 |
| 255 | 40.4 |

Nine human volunteers receive a dose of fentanyl in a DDDS 120. The DDDS 120 comprised a commercially available dermal fentanyl patch, Duragesic-50® (designed to deliver an average of 50 micrograms of fentanyl per hour), distributed by Janssen Pharmaceutica, Inc. of Piscataway, N.J., USA. The experiment was conducted to determine fentanyl concentrations within the volunteers' blood (over a 12 hour period) without heating the DDDS 120 and with heating the DDDS 120 (with the temperature control apparatus 100 described above). The experiments were conducted with at least a two week time period between the heated and unheated sessions. In the unheated session, the DDDS 120 was applied onto the volunteer's chest skin and removed after about 240 minutes. In the heated session, the DDDS 120 was applied onto the subject's chest skin and immediately cover by the temperature control apparatus 100. Both the DDDS 120 and the temperature control apparatus 100 were removed after about 240 minutes. In both sessions, blood samples were taken at various intervals for 12 hours and the fentanyl concentrations in serum samples were determined by radioimmunoassay.

Figure 6:
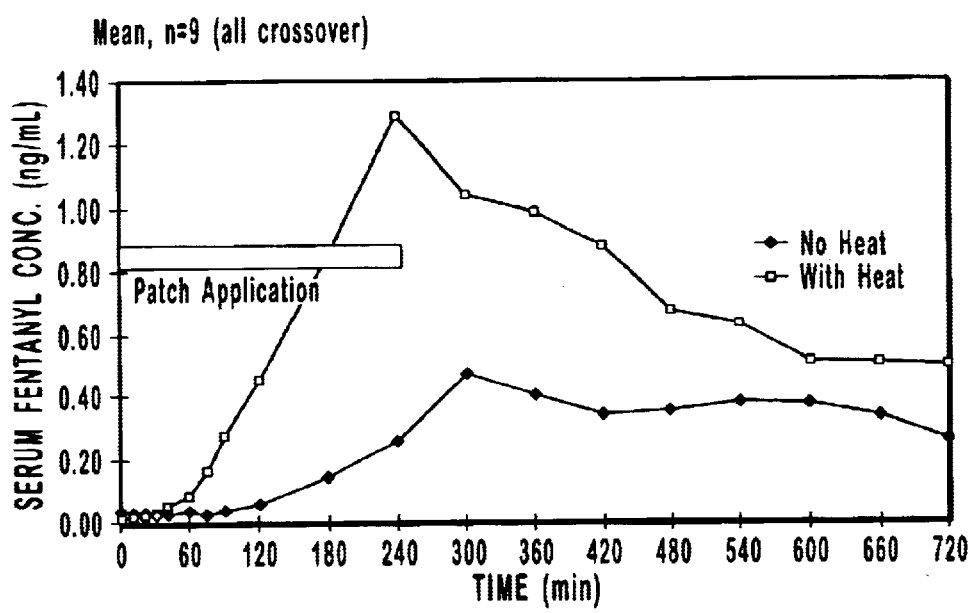
FIG. 6 is a graph of the mean fentanyl concentration of nine volunteers verse time for a four hour contact of a fentanyl containing DDDS with heating and without heating according to the present invention.

FIG. 6 and Table B illustrates the mean serum fentanyl concentrations produced by the heated and unheated Duragesic-50® patches, respectively, over a 720 minute duration (The lowest standard used in the assay was 0.11 ng/ml. Concentrations lower than 0.11 ng/ml were obtained using an extrapolation method.). With heating by the temperature control apparatus 100, it was found that fentanyl began to enter the systemic circulation earlier, and at faster rates. At 240 minutes, the end of the heating and fentanyl patch application, the average serum concentrations of fentanyl in the volunteers with the heating of the Duragesic-50® patch was about 5 times that of the unheated Duragesic-50®. These results demonstrates that controlled heat can significantly increase the speed of dermal fentanyl absorption and shorten the onset time.

TABLE B

| Time (minutes) | Serum Fentanyl Conc. Without Heat (ng/ml) | Serum Fentanyl Conc. With Heat (ng/ml) |
| --- | --- | --- |
| 0 | 0.04 | 0.01 |
| 10 | 0.03 | 0.01 |
| 20 | 0.03 | 0.02 |
| 30 | 0.03 | 0.03 |
| 40 | 0.03 | 0.06 |
| 60 | 0.04 | 0.09 |
| 75 | 0.03 | 0.16 |
| 90 | 0.04 | 0.28 |
| 120 | 0.06 | 0.45 |
| 180 | 0.14 | 0.85 |
| 240 | 0.26 | 1.29 |
| 300 | 0.47 | 1.04 |
| 360 | 0.40 | 0.98 |
| 420 | 0.33 | 0.88 |
| 480 | 0.35 | 0.67 |
| 540 | 0.38 | 0.63 |
| 600 | 0.37 | 0.51 |
| 660 | 0.33 | 0.50 |
| 720 | 0.26 | 0.49 |

Thus, it is believed that the increased temperature increases the skin permeability (compared with a DDDS without such a heating mechanism), which results in the fentanyl entering the patient's systemic circulation faster. This should result in serum fentanyl concentrations reaching steady state quicker. The heating is also believed to increase the body fluid circulation and blood vessel wall permeability in the sub-skin tissues, and cause fentanyl to spend less time in the sub-skin depot site. As a result, the patient receives the analgesic compound more quickly and receives improved pain relief.

Figure 7:
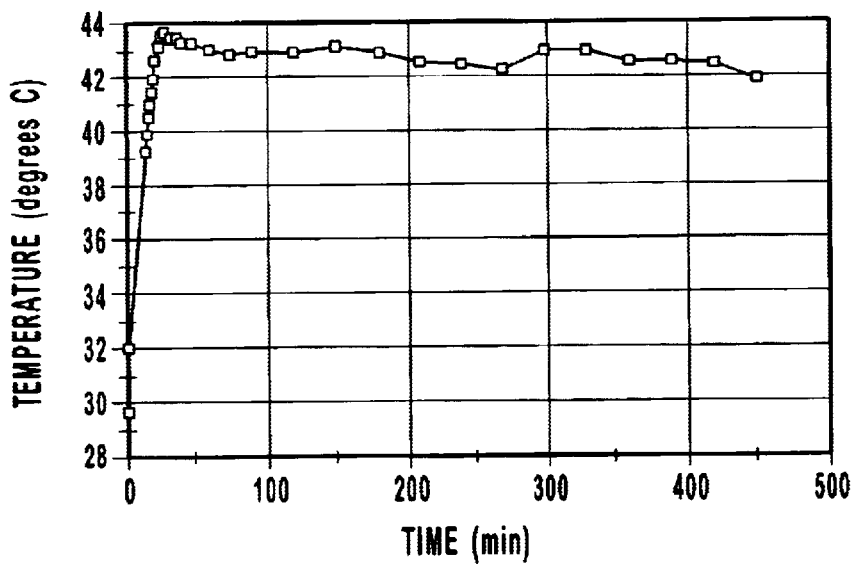
FIG. 7 is a graph of time versus temperature for a temperature control apparatus according to the present invention.

In yet another experiment, the temperature control apparatus 100 comprised the side walls 106 defined by a 3/16 inch thick rectangular foam tape (3 layers of No. 1779 1/16" white foam tape, 3M Corporation, Minneapolis, Minn., USA) with an outer dimension of about 2.25 inches by 4 inches with an opening therein having an inner dimension of about 1.75 inches by 3.5 inches, the bottom wall 102 comprising rectangular medical tape (No. 1525L plastic medical tape, 3M Corporation, Minneapolis, Minn., USA) of a dimension of about 2.25 inches by 4 inches with a non-adhesive side attached to the bottom of the side walls 106, and a top wall 104 comprising a rectangular 1/32 inch thick foam tape (No. 9773 1/32" tan foam tape, 3M Corporation, Minneapolis, Minn., USA) with seventy-eight holes 114 therethrough (diameters approximately 1/32 inch, in a 6 by 13 pattern with about a 6 mm center spacing). The side walls 106, the bottom wall 102, and the top wall 104 define a chamber. The holes 114 of the top wall 104 are covered by an air permeable membrane 116 comprising a porous membrane (No. 9711 CoTran™ membrane, 3M Corporation, Minneapolis, Minn., USA) disposed between the top wall 104 and the temperature regulating mechanism 108. The side walls 106, the bottom wall 102, and the top wall 104 all had 1/8" rounded corners. The temperature regulating mechanism 108 disposed in the chamber comprised a mixture of activated carbon, iron powder, saw dust, sodium chloride and water in the weight ratio of approximately 5:16:3:2:6 weighing approximately 25 grams. This temperature control apparatus 100 was tested on a volunteer's stomach with a temperature probe placed between the temperature control apparatus 100 and the volunteer's skin to measure the temperature. The results of this temperature experiment is illustrated in FIG. 7 and Table C, which shows that the temperature control apparatus 100 is capable of keeping the skin temperature to a narrow, elevated range at between about 41 and 44° C. for extended period of time (at least about 450 minutes).

TABLE C

| Time (minutes) | Temperature (° C.) |
|---|---|
| 0 | 29.6 |
| 1 | 31.9 |
| 15 | 39.3 |
| 16 | 39.9 |
| 17 | 40.6 |
| 18 | 41.0 |
| 19 | 41.4 |
| 20 | 41.9 |
| 22 | 42.7 |
| 24 | 43.2 |
| 26 | 43.6 |
| 28 | 43.7 |
| 30 | 43.5 |
| 35 | 43.5 |
| 40 | 43.3 |
| 45 | 43.3 |
| 60 | 43.1 |
| 75 | 42.9 |
| 90 | 43.0 |
| 120 | 43.0 |
| 150 | 43.2 |
| 180 | 43.0 |
| 210 | 42.6 |
| 240 | 42.5 |
| 270 | 42.3 |
| 300 | 43.0 |
| 330 | 43.0 |
| 360 | 42.6 |
| 390 | 42.6 |
| 420 | 42.5 |
| 450 | 41.9 |

Figure 8:
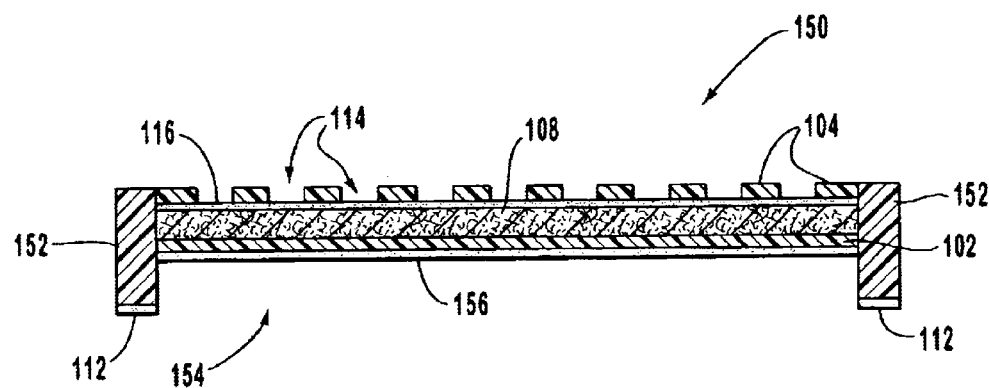
FIG. 8 is a side cross-sectional view of another embodiment of a temperature control apparatus according to the present invention.

FIG. 8 illustrates another embodiment of a temperature control apparatus 150 comprising a temperature regulating mechanism 108 surrounded by a bottom wall 102, a top wall 104, and side walls 152. The side walls 152 extend a distance below the bottom wall 102 to define a cavity 154. The bottom wall 102 is preferably made of plastic tape material and the side walls 152 are preferably made of a flexible non-air permeable material, such as non-air permeable closed-cell foam material. A portion of the bottom of the temperature control apparatus 150 includes an adhesive material 112 on the bottom of the side walls 152 and, preferably, includes a second adhesive material 156 in the bottom of the bottom wall 102, wherein the second adhesive material 156 is preferably less adhesive than the adhesive material 112. Again, the temperature regulating mechanism 108 preferably comprises a composition of activated carbon, iron powder, sodium chloride, water, and, optionally, saw dust. The top wall 104 is preferably also a flexible non-air permeable material having holes 114 therethrough. An air permeable membrane 116 is disposed between the top wall 104 and the temperature regulating mechanism 108 to regulate the amount of air reaching the temperature regulating mechanism 108 through the holes 114.

Figure 9:
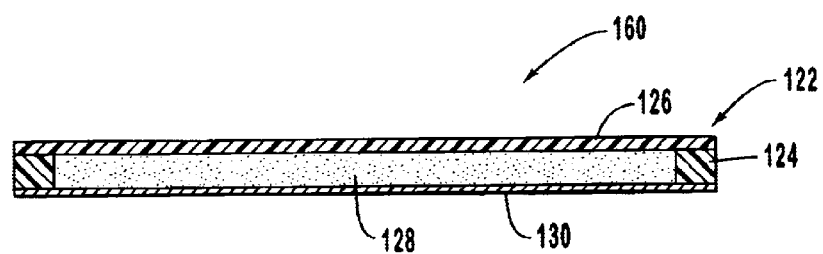
FIG. 9 is a side cross-sectional view of another embodiment of a dermal drug delivery system according to the present invention.

FIG. 9 illustrates a DDDS 160 comprising a housing made 122 of flexible materials. The housing 122 preferably comprises side walls 124 and a top wall 126 with a drug formulation 128 disposed within the housing 122, and may include a membrane 130 which may be a rate-limiting membrane.

Figure 10:
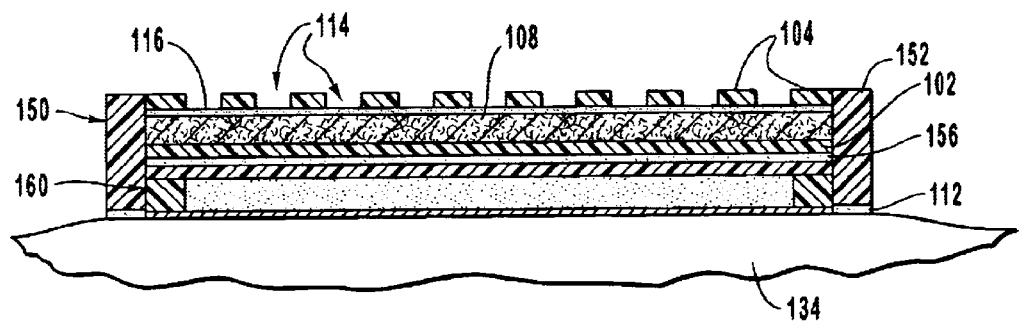
FIG. 10 is a side cross-sectional view of the temperature control apparatus of FIG. 8 in conjunction with the dermal drug delivery system of FIG. 9 according to the present invention.

FIG. 10 illustrates the temperature control apparatus 150 of FIG. 8 attached to the DDDS 160 of FIG. 9. The DDDS 160 is placed on (or attached with an adhesive, not shown) a portion of the skin 134 of a patient and the temperature control apparatus 150 is placed over the DDDS 160, such that the DDDS 160 resides within the cavity 154 (see FIG. 8). The adhesive material 112 attaches to the skin 134 and holds the temperature control apparatus 150 in place. If the DDDS 160 is not attached to the skin 134, the temperature control apparatus 150 holds the DDDS 160 in place. Preferably, the DDDS 160 is attached to the skin 134 with an adhesive material (not shown) with the temperature control apparatus 150 placed over the DDDS 160. The temperature control apparatus 150 is attached to the skin 134 with the adhesive material 112 and the second adhesive material 156 (less adhesive than any attachment adhesive (not shown) between the DDDS 160 and the skin 134 and less adhesive than the adhesive material 112 between the temperature control apparatus 150 and the skin 134) attaches the temperature control apparatus 150 to the DDDS 160. Such an arrangement results in secure adhesion of the temperature control apparatus 150 and the DDDS 160 to the skin 134, yet allows for the removal of the temperature control apparatus 150 without removing the DDDS 160.

Figure 11:
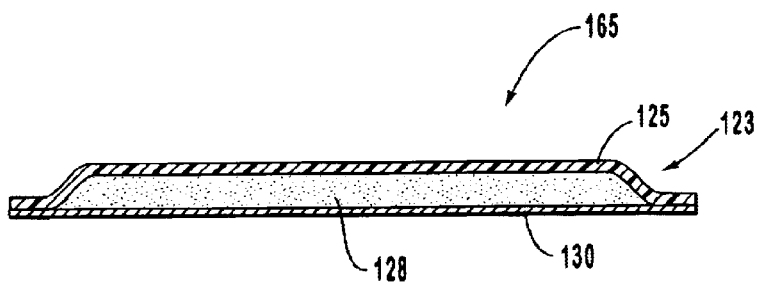
FIG. 11 is a side cross-sectional view of still another embodiment of a dermal drug delivery system according to the present invention.
Figure 12:
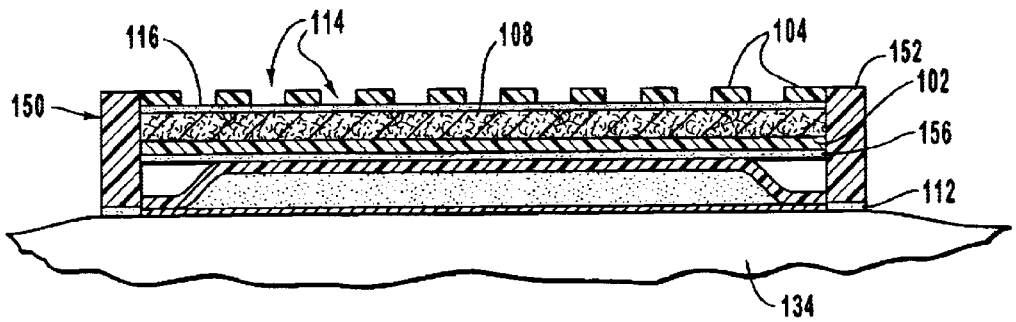
FIG. 12 is a side cross-sectional view of the temperature control apparatus of FIG. 8 in conjunction with the dermal drug delivery system of FIG. 1 according to the present invention.

FIG. 11 illustrates an alternate DDDS 165 comprising a housing 123 made of flexible material(s). The housing 123 preferably comprises top wall 125 and a membrane 103, which may be a rate-limiting membrane, with a drug formulation 128 disposed within the housing 123. FIG. 12 illustrates the temperature control apparatus 150 of FIG. 8 attached to the DDDS 165 of FIG. 11, similar that described for FIG. 10.

EXAMPLE 2

An example of using the embodiment of the present invention illustrated in FIGS. 8–12 for administering analgesic material to treat breakthrough pain consists of a patient or care giver placing the DDDS 160, 165 on the skin 134 of the patient with the temperature control apparatus 150 placed thereover. By way of example, when the DDDS 160, 165 is a commercially available fentanyl patch, Duragesic-50®, it takes several hours after the application of the DDDS 160, 165 to obtain a sufficient steady state level of fentanyl in the patient's bloodstream to control baseline pain. However, such as with the treatment of cancer patients, a patient will from time to time suffer breakthrough pain, which is a suddenly increased but usually not long lasting pain. When a patient feels that a breakthrough pain episode is imminent, the patient places the temperature control apparatus 150 over the DDDS 160, 165. The heat from the temperature control apparatus 150 increases the temperature of the fentanyl patch, the skin, and tissues under the skin. As a result, more fentanyl is absorbed across the skin. Furthermore, fentanyl already in the skin and sub-skin depot sites (i.e., fentanyl molecules that have already permeated across the skin but were stored in the skin and sub-skin tissues) starts to be released into the systemic circulation at faster rates because of increased blood/body fluid flow in the tissues under the fentanyl patch and increment blood vessel wall permeability caused by heat from the temperature control apparatus 150. The overall result is that fentanyl concentration in the patient's bloodstream is significantly increased shortly after the heating patch is applied (compared with no temperature control apparatus 150 being used), and the increased fentanyl in the bloodstream alleviates the breakthrough pain in a timely manner. It is believed that for lipophilic compounds, such as fentanyl, that usually have significant dermal depot effect (storage in depot sites in the skin and sub-skin tissues and gradual release from the depot sites), the increased drug release from the depot sites due to the heating may make a more rapid and a more significant contribution to increasing bloodstream drug concentrations than the contribution from increased skin permeability caused by the heat. The patient can leave the heating patch on for a pre-determined length of time, based on his previous experience of breakthrough pain, before he stops the heating by removing the patch or placing an air impermeable tape to cover all the holes on the top wall 104. The patient may also stop the heating when he feels the current episode of breakthrough pain is over or beginning to end.

Preferably, the heating patch is designed to have a pre-determined heating duration that is sufficient to treat most patients' breakthrough pain, but not long enough to cause serious side effects associated with fentanyl overdose. However, if a particular patient has a higher tolerance to fentanyl, the patient can use two or more of the heating patches consecutively so that the patient gets just enough extra fentanyl to treat the breakthrough pain.

EXAMPLE 3

Another example of using the embodiment of the present invention illustrated in FIGS. 8–12 for dermally administering nicotine for suppressing nicotine craving consists of a user placing a nicotine DDDS 160, 165 on the skin 134. After a few hours, the user should obtain a steady state nicotine concentration in the bloodstream that is sufficient to suppress a "baseline" nicotine craving. When the user starts to have an episode of increased nicotine craving, the user puts the temperature control apparatus 150 on top of the DDDS 160, 165. The temperature control apparatus 150 preferably heats for at least 15 minutes before the exothermic reaction exhausts the temperature regulating mechanism 108. The heat increases the transport of nicotine across the skin, and increases the blood flow in the tissues under the DDDS 160, 165 which carries nicotine stored in the tissues under the DDDS 160, 165 into the systemic circulation at increased rates. As a result, the user gets a rapid increase in his blood nicotine concentration to treat the surge of the nicotine craving. After the heating, the nicotine absorption rates gradually come back to normal to deliver the steady state nicotine concentration in the bloodstream.

EXAMPLE 4

Another example of using the embodiment of the present invention illustrated in FIGS. 8–12 for dermally administering testosterone to increase and optimize the amount of drug delivered consists of a user placing the DDDS 160, 165, such as a once a day dermal testosterone patch, for example Androderm® produced by Theratech, Inc. of Salt Lake City, Utah, USA, on the skin 134. The DDDS 160, 165 is generally applied to the skin 134 at night, for example at 10 PM. However, if the user does not get a sufficient dosage of testosterone the next day, the user puts the temperature control apparatus 150 on top of the DDDS 160, 165. The increased temperature in the DDDS 160, 165, the skin 134 and tissues under the skin significantly increase the dermal absorption of testosterone. In addition, if the DDDS 160, 165 has permeation enhancer, such as glycerol monooleate, the heat should also make the enhancer permeate the skin faster, thus making it more effective. The ultimate result is that the user gets sufficient testosterone from the DDDS 160, 165. Furthermore, the user may also place the temperature control apparatus 150 on the DDDS 160, 165 in the morning to deliver more testosterone from morning to the evening when the user needs the higher dosage the most. The increased absorption of testosterone by the controlled heating may allow the readuction of a permeation enhancer concentration which is used in the DDDS 160, 165. In a testosterone DDDS, a permeation enhancer is usually necessary for delivering sufficient testosterone, however permeation enhancers may cause serious skin irritation, such as glycerol monooleate in Androderm®.

EXAMPLE 5

It is, of course, understood that the DDDS 160, 165 and the temperature control apparatus 150 can be with athletic injuries. For example, if a person injures an elbow in a sporting event or such, the user can apply a DDDS 160, 165 containing an analgesic, such a dexamethasone, wintergreen oil, or the like, wherein the DDDS 160, 165. The heat generated by the temperature control apparatus 150 drives more drug into the elbow and the increased the blood flow induced by the heat takes the drug deeper into the elbow.

EXAMPLE 6

Yet another example of using the embodiment of the present invention illustrated in FIGS. 8–12 comprises using the temperature control apparatus 150 for administering analgesic material to treat pain when the diffusion coefficient of the active ingredients in the formulation 128 and/or permeability coefficient across a rate limiting membrane 130 is so low that it dominantly determines the overall absorption rate of analgesic material from the DDDS 160, 165 into a patient's body. By way of example with the use of a DDDS 160, 165, the patient or care giver places the DDDS 160, 165 on the skin 134 of the patient. If after a time of wearing the DDDS 160, 165, it is determined that for this particular patient and his conditions a higher concentration of fentanyl in the bloodstream is required to properly treat his pain, the temperature control apparatus 150 is placed on top of the DDDS 160, 165 to heat the DDDS 160, 165.

The increased temperature increases diffusion coefficient of the active ingredient in the formulation in the DDDS 160, 165 and increases the permeability coefficient across the rate limit membrane 130 in the DDDS 160, 165, and, thus, the overall rates at which the active ingredient enters the patient's body. This, in turn, increases the concentration of active ingredient in the bloodstream. As a result, the patient gets the increased and proper effect.

EXAMPLE 7

Still another example of using the embodiment of the present invention illustrated in FIGS. 8–12 comprises using the temperature control apparatus 150 for decreasing onset time of an analgesic material from the DDDS 160, 165. By way of example with the use of a commercially available fentanyl patch, such as Duragesic-50®, as the DDDS 160, 165, the patient or care giver places the DDDS 160, 165 on the skin 134 of the patient and places the temperature control apparatus 150 over the DDDS 160. Preferably, the temperature control apparatus 150 includes a sufficient amount of activated carbon, iron powder, sodium chloride, and water in the temperature regulating mechanism 108 to sustain an exothermic reaction for at least 4 hours.

The heat from the temperature control apparatus 150 increases the temperature at a contact surface of the skin 134 and the DDDS 160, 165 to temperatures up to about 60° C., preferably a narrow temperature range between about 36° C. and 46° C., most preferably between 37° C. and 44° C., and maintains this temperature for a period of time (i.e., approximately 4hours). During this time, the heat increases the speed of fentanyl release from the DDDS 160, 165, the permeation rate across the skin 134, and the speed of blood circulation which carriers the fentanyl into the systemic circulation faster. After the exothermic reaction ceases (approximately 4 hours), the fentanyl absorption and concentration in the bloodstream begins to decrease from the elevated levels caused by the heat from the DDDS 160, 165 returns to normal (unheated) levels. The patient continues to wear the system for a total of between about 48 and 72 hours. Compared with a DDDS 160, 165 without the use of the temperature control apparatus 150, the fentanyl begins to appear in the bloodstream significantly earlier to yield a shortened onset time and the fentanyl concentrations in the bloodstream in the early hours of application are significantly higher than that produced by an unheated DDDS 160, 165. The therapeutic serum fentanyl concentration varies from person to person. For example some people respond to levels above 0.2 ng/mL. Referring to FIG. 6, this 0.2 ng/mL concentration is achieved in about one-third the amount of time for a heated system than for a non-heated system (i.e., about 70 minutes as compared with about 210 minutes).

After a period of time when the exothermic reaction of temperature control apparatus 150 slowly stops generating heat, the fentanyl concentration in the bloodstream starts to gradually approach the normal steady state fentanyl concentrations in the bloodstream which would ultimately be seen with an unheated DDDS 160, 165, given a sufficient amount of time. As a result, the temperature control apparatus 150 significantly shortens the onset time of Duragesic-50® without significantly altering its steady state delivery rates. Thus, the important advantage provided by this approach is that the onset time of a DDDS 160, 165 already in clinical use can be shortened without significantly altering its steady state delivery rates which are not only adequate, but also familiar to the caregivers and the patients.

EXAMPLE 8

A further example of using the embodiment of the present invention illustrated in FIGS. 8–12 comprises using the temperature control apparatus 150 for a sustained high absorption rate of an analgesic material from the DDDS 160, 165.

Cancer patient's tend to develop a tolerance for fentanyl (and other analgesic materials) after extended use. For example, if a patient becomes tolerant to a Duragesic-100® (100 micrograms/hour deliver rate) dermal patch, a care giver may apply both a Duragesic-100® and a Duragesic-50® (50 micrograms/hour delivery rate) to treat the patient's cancer pain. However, instead of using two Duragesic® patches, a care giver can use a Duragesic-75® (75 micrograms/hour delivery rate) patch in conjunction with the temperature control apparatus 150, preferably designed to last between about 12 and 24 hours, to increase the fentanyl absorption. The care giver replaces the heating patch, after the designed heating during is over, with another heating patch to maintain a desired temperature, and continues to do so until the fentanyl in the Duragesic-75® patch can no longer supply a therapeutic amount of fentanyl. It is, of course, understood that the temperature control apparatus 150 may be designed to last as long as the expected usage time of the Duragesic-75® dermal patch.

Heating patches with different heating temperatures may be used to achieve different increased levels of fentanyl deliver rates.

EXAMPLE 9

Yet still another example of using the embodiment of the present invention illustrated in FIGS. 8–12 again comprises using the temperature control apparatus 150 for decreasing onset time of an analgesic material from the DDDS 160, 165. By way of example, a local anaesthetic, such as a eutectic mixture of lidocaine and tetracaine, can be administer with a DDDS 160, 165 to numb the skin 134 before a painful medical procedure. A faster onset and deeper numbing effect within a short time can be achieved by placing the temperature control apparatus 150 over the DDDS 160, 165, wherein the temperature control apparatus 150 is capable of providing heating the skin to a narrow range between about 37° C. and 41° C., preferably between 39° C. and 40° C., for at least 30 minutes. The skin 134 should be numb in 30 minute or less, which is much shorter than that without heating. Depending on the original skin temperature, it is believed that such heating will reduce the onset time by about 60% of the onset time without heating.

EXAMPLE 10

Still another example of using the embodiment of the present invention illustrated in FIGS. 8–12 again comprises using the temperature control apparatus 150 for increasing the solubility of an analgesic from the DDDS 160, 165. By way of example, a formulation may be designed to contain an analgesic which has such low solubility in the formulation that a significant portion is in the form of undissolved paritcles, and the solubility increases with increasing the temperature of the formulation.

A patient places such a DDDS 160, 165 on his skin. If the amount of the analgesic compound the patient receives from the DDDS 160, 165 is not sufficient, the patient places the temperature control apparatus 150 on or over the DDDS 160, 165. The heat generated in the temperature control apparatus 150 increases the temperature of the formulation in the DDDS 160, 165 and maintains the increased temperature for a significant part or substantially the entire length of the DDDS 160, 165 application. The increased temperature in the formulation increases the solubility of the analgesic compound in the formulation. Consequently, more analgesic compounds are dissolved in the formulation which gives higher driving force for the transdermal permeation of the analgesic compound. As a result, more of the analgesic compound enters the patient's body.

Another variation of this example is for the treatment of breakthrough pain. If the solubility of the analgesic compound in a formulation in the DDDS 160, 165 is sufficient to treat baseline pain, but not breakthrough pain, a patient can place the temperature control apparatus 150 on or over the DDDS 160, 165 when an episode of breakthrough pain occurs. The increased solubility of the analgesic compound in the formulation results in the patient obtaining more analgesic compound to treat the breakthrough pain. The heating from the temperature control apparatus can be discontinued after the patient determines that the pain is under control.

Although Examples 1–10 discuss the application of specific drugs, it is, of course, understood that the present invention is not limited to any particular drug(s). It is understood that a considerable variety of drugs classes and specific drugs may be used with the present invention. The drug classes can include without limitation androgen, estrogen, non-steroidal anti-inflammatory agents, anti-hypertensive agents, analgesic agents, anti-depressants, antibiotics, anti-cancer agents, local anesthetics, antiemetics, anti-infectants, contraceptives, anti-diabetic agents, steroids, anti-allergy agents, anti-migraine agents, agents for smoking cessation, and anti-obesity agents. Specific drugs can include without limitation nicotine, testosterone, estradiol, nitroglycerin, clonidine, dexamethasone, wintergreen oil, tetracaine, lidocaine, fentanyl, sufentanil, progestrone, insulin, Vitamin A, Vitamin C, Vitamin E, prilocaine, bupivacaine, sumatriptan, and dihydroergotamine.

EXAMPLE 11

Yet still another example of using the embodiment of the present invention illustrated in FIGS. 8–12 again comprises using the temperature control apparatus 150 for maintaining a stable temperature for the DDDS 160, 165. Certain drugs have relatively low therapeutic indices, meaning that the differences between the therapeutic dose and the dose which can cause serious and/or undesired side effects are small. Thus, dermal delivery of such drugs can be dangerous (over-dose) or ineffective (under-dose), especially for individuals whose skin are exposed to highly variable ambient temperatures, such as people working outdoors in extreme weather conditions. The variations in ambient temperature can cause variations in skin temperature which can significantly change the ultimate dermal absorption of the drugs. Covering a DDDS 160, 165 containing a low therapeutic indices drug with the temperature control apparatus 150 can regulate the skin temperature to a narrower range and reduce the variation in dermal drug absorption. Drugs and classes of drugs that may benefit from this method include, but are not limited to, drugs such as nicotine, nitroglycerin, clonidine, fentanyl, sufentanil, and insulin; and classes of drugs such as non-steroidal anti-inflammatory agents, anti-hypertensive agents, analgesic agents, anti-diabetic agents, and anti-migraine agents.

Figure 13:
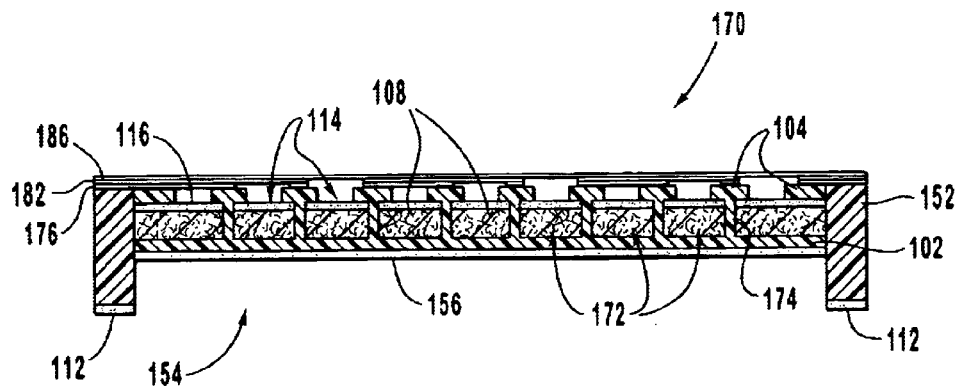
FIG. 13 is a side cross-sectional view of yet another embodiment of a temperature control apparatus having three cover layers over an oxygen activated temperature regulating mechanism chambers according to the present invention.
Figure 14:
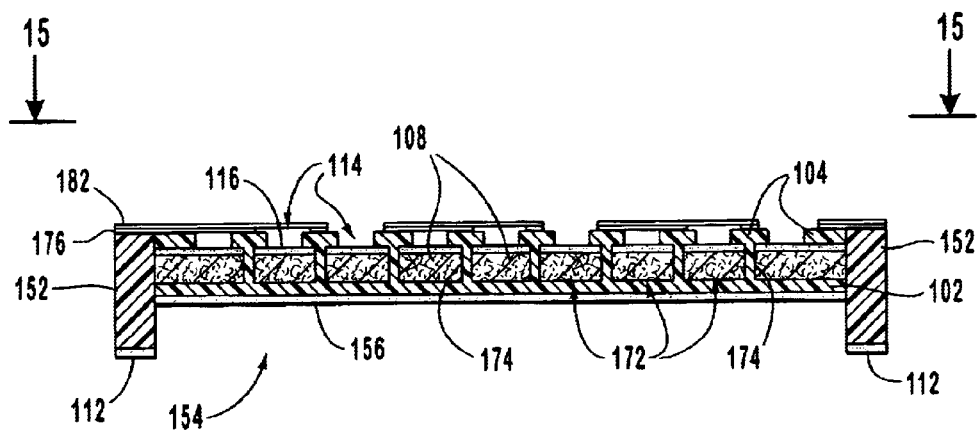
FIG. 14 is a side cross-sectional view of the temperature control apparatus of FIG. 13 having a first cover layer removed according to the present invention.
Figure 15:
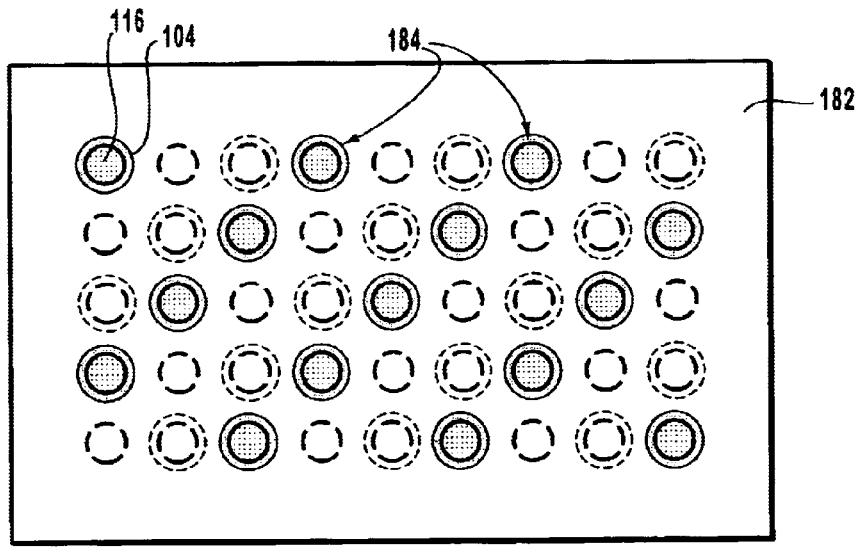
FIG. 15 is a top plan view of the temperature control apparatus of FIG. 14 along line 15—15 according to the present invention.
Figure 16:
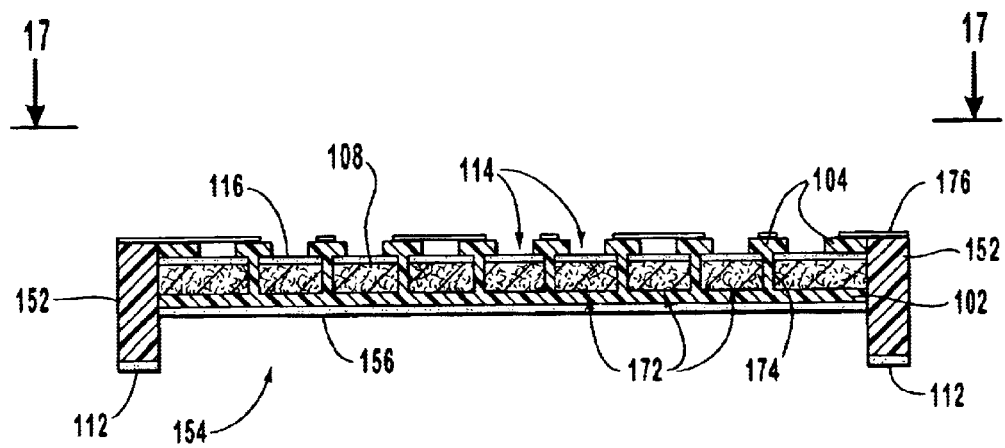
FIG. 16 is a side cross-sectional view of the temperature control apparatus of FIG. 14 having a second cover layer removed according to the present invention.
Figure 17:
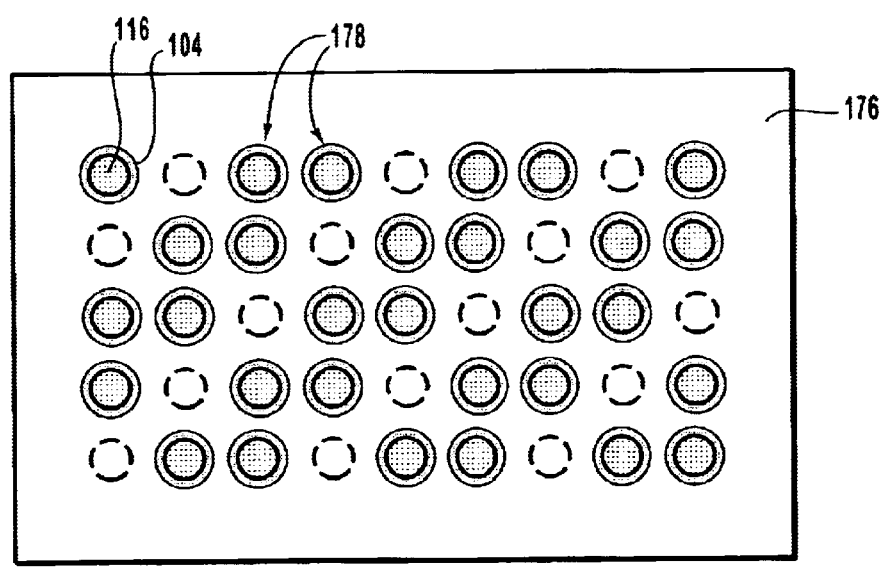
FIG. 17 is a top plan view of the temperature control apparatus of FIG. 16 along line 17—17 according to the present invention.
Figure 18:
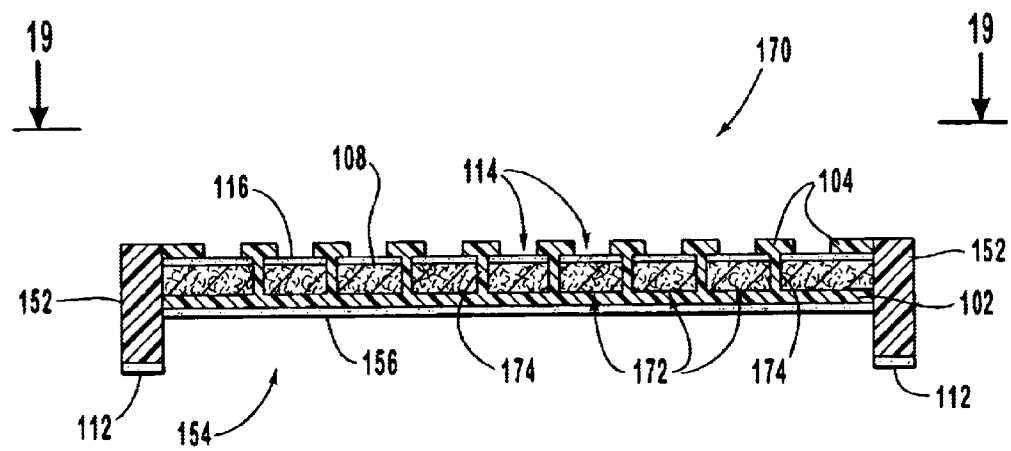
FIG. 18 is a side cross-sectional view of the temperature control apparatus of FIG. 16 having a third cover layer removed according to the present invention.
Figure 19:
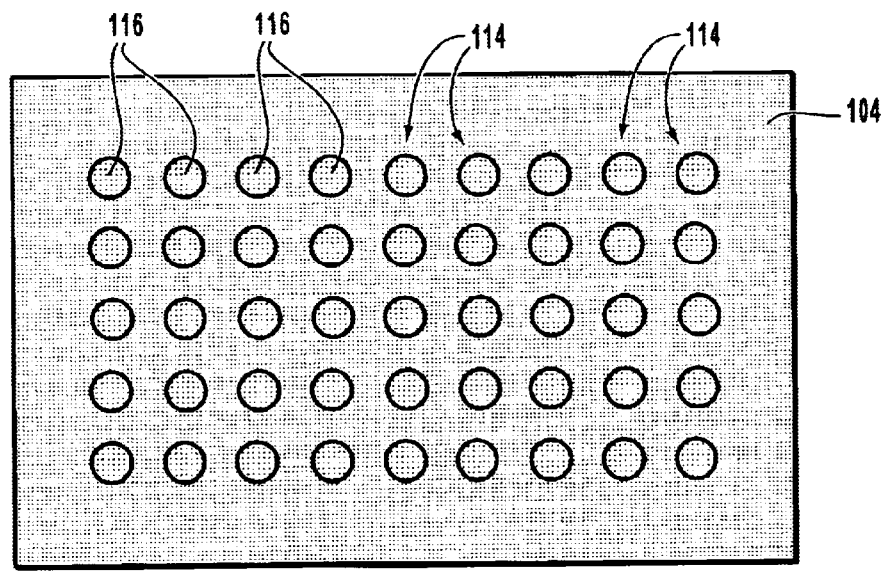
FIG. 19 is a top plan view of the temperature control apparatus of FIG. 18 along line 19—19 according to the present invention.

FIGS. 13–19 illustrates another embodiment of a temperature control apparatus 170. FIG. 13 illustrates the temperature control apparatus 170 which is similar to the embodiment of FIG. 8, but comprises a temperature regulating mechanism 108 which is made up of a plurality of chambers 172 separated by non-air permeable walls 174. The temperature regulating mechanism 108 is substantially surrounded by a bottom wall 102, a top wall 104, and side walls 152. Again, the temperature regulating mechanism 108 preferably comprises a composition of activated carbon, iron powder, sodium chloride, water, and, optionally, saw dust, which is disposed in each of the chambers 172. The top wall 104 is preferably also a flexible non-air permeable material having a plurality of holes 114 therethrough, preferably, a row of holes 114 for each chamber 172. An air permeable membrane 116 is disposed between the top wall 104 and the temperature regulating mechanism 108 to regulate the amount of air reaching the temperature regulating mechanism 108 through the holes 114. The top wall 104 can have at least one cover covering the plurality of holes 114 for the regulation of the air into the chambers 172. As illustrated in FIG. 13, three covers are layered on the top wall 104. A first cover layer 176 is affixed to the top wall 104 and has openings 178 (see FIG. 17) to expose 2out of 3holes 114. A second cover layer 182 is affixed to the first cover layer 176 and has opening 184 (see FIG. 15) to expose 1 out of 3 holes 114. A top cover 186, which has no openings, is affixed to the second cover layer 182. Thus, a patient has a various opinions on what percentage of chambers 172 to expose to ambient air. If the heat generated from one third of the chambers is required, the top cover 186 is removed, as shown in FIGS. 14 and 15. If the heat generated from two thirds of the chambers is required or if another additional heat is needed after the depletion of the first one-third of the temperature regulating mechanism 108, the top cover 186 and the second cover layer are removed, as shown in FIGS. 16 and 17. If the heat generated from all of the chambers is required or if another additional heat is needed after the depletion of the first and second one-third of the temperature regulating mechanism 108, the top cover 186, the second cover layer 182, and the first cover layer 176 are removed, as shown in FIGS. 18 and 19. It is, of course, understood that more or less cover layers can be used with any number of holes to results in any desired amounts of the temperature regulating mechanism 108 being activated.

Thus, by way of example a patient can have a number of choices in using the temperature control apparatus 170, such for the suppression of breakthrough pain. When the breakthrough pain occurs, the patent places the temperature control apparatus 170 over an analgesic material DDDS and can do any of the following:

1) Activate a particular number or percent of chambers 172 by removing the requisite covers depending on how much additional analgesic material is required to treat the breakthrough pain. The covers can be preferably replaced to stop the exothermic reaction when no more additional analgesic material is required.

2) Activate a particular number or percent of chambers 172, exhaust the heat generating capacity of those chambers 172, and then activate other (non-activated) chambers 172. This extends the heating duration of the temperature control apparatus 170. The duration of the total heating time is determined by the typical duration of the particular patient's breakthrough pain.

3) Activate enough chambers 172 to treat one episode of breakthrough pain, and leave the heating patch in place. When the next episode of breakthrough pain occurs, activate unused chambers 172.

Figure 20:
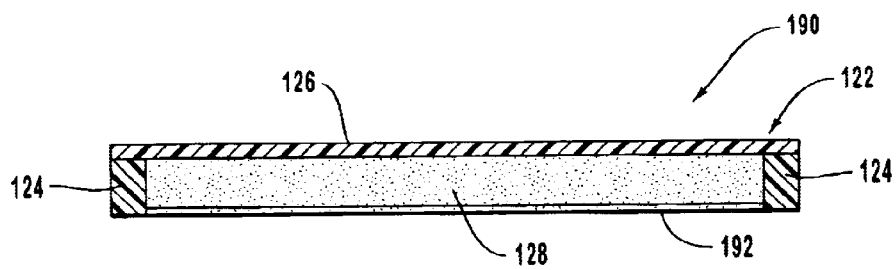
FIG. 20 is a side cross-sectional view of another embodiment of a dermal drug delivery system having a rate limiting membrane according to the present invention.

FIG. 20 illustrates a dermal drug delivery system 190 (hereinafter "DDDS 190") having a rate limiting membrane 192. The structure of DDDS 190 is similar to that of FIG. 3. However, the DDDS 190 includes a rate limiting membrane 192 which resides between the drug formulation 128 and the skin 134 of a patient.

Generally, the permeability of the drug in the drug formulation 128 through the rate limiting member 192 is significantly lower than the permeability of the drug in the drug formulation 128 into the skin of an average patient. Rate limiting membranes 192 are used to minimize the variation in overall permeation, and to regulate the amount of drug delivered to the patient so that overdosing does not occur. Another aspect of the present invention is the use of a temperature sensitive rate limiting membrane, such that the drug permeation rate through the rate limiting membrane increases significantly with increasing temperature. With such a DDDS 190, the above discussed temperature control mechanisms 100 (FIG. 1 & 2), 150 (FIG. 8), and 170 (FIG. 13) can be used to increase the drug delivery rate across the rate limiting membrane 192 to treat breakthrough pain, reduce onset time, increase steady state delivery rate, or other advantages discussed above.

Figure 21:
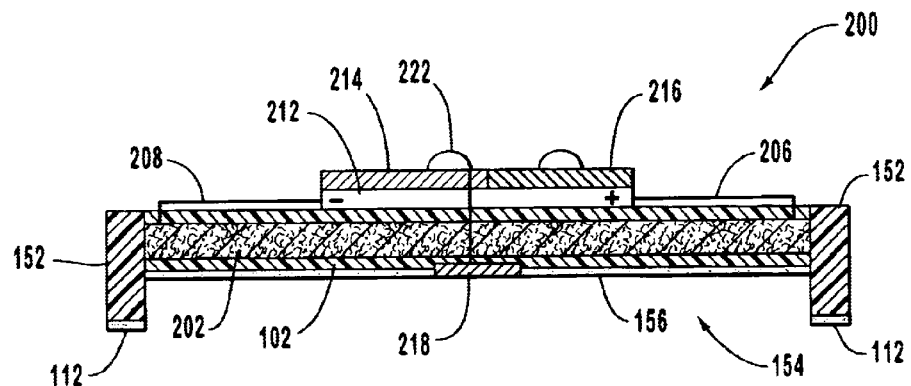
FIG. 21 is a side cross-sectional view of an electric temperature control mechanism according to the present invention.

The possible temperature control mechanisms are not limited to the exothermic reaction mixture of iron powder, activated carbon, salt, water, and sawdust, as discussed above. FIG. 21 illustrates an electric temperature control mechanism 200 comprising an electric heating element 202 surrounded by a bottom wall 102, a top wall 104, and side walls 152 (similar to FIG. 8). The side walls 152, preferably, extend a distance below the bottom wall 102 to define a cavity 154. It is, of course, understood that the electric heating element 202 does not have to have the side walls 152 forming a cavity 154.

The bottom wall 102 and the side walls 152 are preferably made of a flexible non-air permeable material, such as non-air permeable closed-cell foam material. A portion of the bottom of the temperature control apparatus 200 includes an adhesive material 112 on the bottom of the side walls 152 and, preferably, includes a second adhesive material 156 in the bottom of the bottom wall 102, wherein the second adhesive material 156 is preferably less adhesive than the adhesive material 112. The electric heating element 202 preferably comprises a flexible resistor plate that can generate heat when supplied with an electric current through traces 206, 208. The electric current is preferably supplied from a battery 212 attached to a control mechanism 214, and an electronic switch 216. The battery 212, the control mechanism 214, and the electronic switch 216 are preferably attached to the top surface of the top wall 104. The electric heating element 202 is activated by triggering the electronic switch 216 which begins the flow of electric current from the battery 212 to the electric heating element 202. A temperature sensor 218, such as a thermistor, is preferably attached to the bottom of the bottom wall 102 and sends a signal (corresponding to the temperature at the bottom of the bottom wall 102) through electric trace 222 to the control mechanism 214. The control mechanism 214 regulates the flow of current to the electric heating element 202, so that the electric heating element 202 quickly brings the temperature at a contact surface between the bottom wall 102 and a top of a DDDS (not shown) to a pre-determined level and maintains the temperature at that pre-determined level. The following features may be incorporated into the control mechanism 214: 1) a mechanism that allows a physician or care giver set the length of each heating period for each patient, which allows the physician to limit the heating, and hence the extra drug that the patient can get based on the conditions of the patient; 2) a mechanism that allows the physician or care giver to set the minimum time between the heating periods, and hence how often the patient can get the extra drug through increase heat; 3) a mechanism that allows the physician or care giver to set a pre-determined temperature; and/or 4) a mechanism that allows the physician or care giver to control the heating temperature profile, such as gradually increasing heating temperature or decreasing temperature over a pre-determined period of time. These features can potentially give simple DDDSs a variety of control options for the physician and/or the patient on the quantity and timing of the delivery of extra drug.

EXAMPLE 12

An example of using the embodiment of the present invention, such as illustrated in FIG. 21, includes using the temperature control mechanism 200 for decreasing onset time of a local anesthetic comprising approximately 14% tetracaine/lidocaine eutectic mixture by weight; 8.6% polyvinyl alcohol (PVA) by weight, 0.17% sodium hydroxide (NaOH) by weight, and the remainder water ($H_2O$. The local anesthetic, in the form of a thin patch, was placed on a volunteer's left forearm and the temperature control mechanism 200, set to maintain a 41° C. temperature, was placed over the local anesthetic. The local anesthetic was also placed on a volunteer's right forearm (at a different time) and left at room temperature (about 24° C.). The results are presented in Table D, wherein the effect of the local anesthetic was measure by a pain score when the skin is poked by a blunt object. The pain score is defined as follows:

| Score | Effect |
| --- | --- |
| 0 | No effect |
| 1 | Between no numbness and medium numb |
| 2 | Medium numb |
| 3 | almost completely numb |
| 4 | completely numb, but not deep |
| 5 | completely numb and deep |

TABLE D

| Time (minutes) | Pain Score with Heating | Pain Score w/o Heating |
| --- | --- | --- |
| 15 | 4 | 2 |
| 20 | 5 | 3 |
| 25 |   | 4 |
| 30 |   | 5 |

Thus, it can be seen that heating reduced the onset time of complete and deep numbness by approximately 33%.

EXAMPLE 13

Another example of using the embodiment of the present invention, such as illustrated in FIG. 21, includes using the temperature control mechanism 200 for a sustained high absorption rate of an analgesic material from the DDDS 160, 165. Cancer patient's tend to develop a tolerance for fentanyl (and other analgesic materials) after extended use. For example, if a cancer patient becomes tolerant to a Duragesic-100® (100 micrograms/hour deliver rate) dermal patch, a care giver may apply an electric heating device, such as temperature control mechanism 200, on a Duragesic-100® patch and sets the temperature to heat the skin surface to 38° C. to obtain a higher rate of fentanyl delivery from the Duragesic-100® patch for treating the patient's cancer pain. However, if, after a duration of treatment, the cancer patient becomes tolerant the fentanyl delivery rate at 38° C., the care giver can adjust the temperature control mechanism 200 on the of Duragesic-100® patch to heat the skin surface to 40° C. to obtain an even higher rate of fentanyl delivery from the Duragesic-100® patch for treating the patient's cancer pain.

Figure 22:
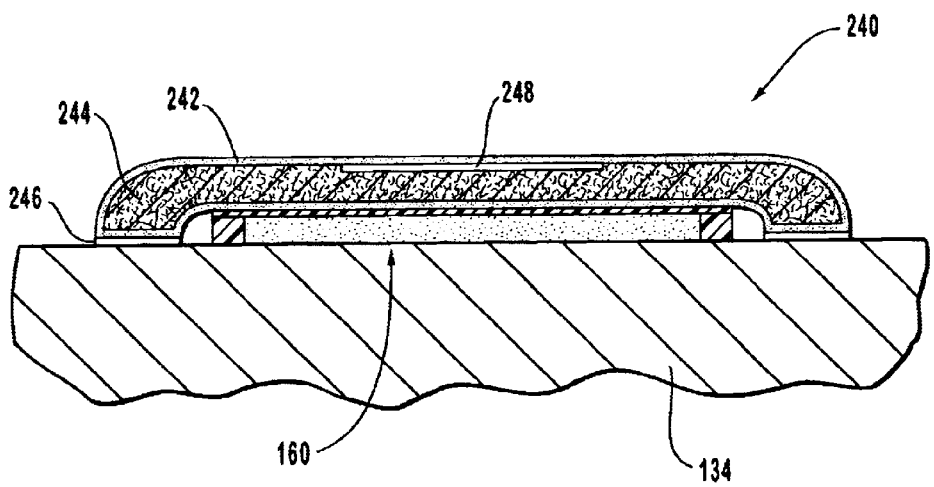
FIG. 22 is a side cross-sectional view of a temperature control apparatus comprising a flexible bag filled with a supercooled liquid according to the present invention.

FIG. 22 illustrates another embodiment of a temperature control apparatus 240 comprising a substantially flat, flexible bag 242 filled with a supercooled liquid 244, such as a concentrated solution of sodium acetate. A bottom portion of the bag 242, preferably, includes an adhesive material 246. The bag 242 is preferably slightly larger than the DDDS 160 such that the adhesive material 246 may contact and adhere to the skin 134. The bag 242 further includes a triggering mechanism 248, such as a metal strip. For example, when a patient wearing a DDDS containing an appropriate analgesic material feels the imminent onset of breakthrough pain, the bag 242 is placed over the DDDS 160. The triggering mechanism 248 is activated (such as by bending a metal strip) which triggers crystallization in the supercooled liquid. The heat generated by the crystallization (phase transition) increases the speed of transport of analgesic material into the body and the speeds the release of analgesic material from the depot sites in the skin and the sub-skin tissues. As a result the patient gets a rapid delivery of extra analgesic material to treat breakthrough pain. Usually, the heat generated by a phase transition can not be sustained over extended time, but may be enough to release adequate amount of analgesic material from the depot sites in the tissues under the skin to treat the breakthrough pain. The advantage of the temperature control apparatus 240 is that it is reusable. After use, the temperature control apparatus 240 can be placed in hot water and then cooled to room temperature to transfer the solidified contents in the bag back to a supercooled liquid 244.

EXAMPLE 14

Figure 23:
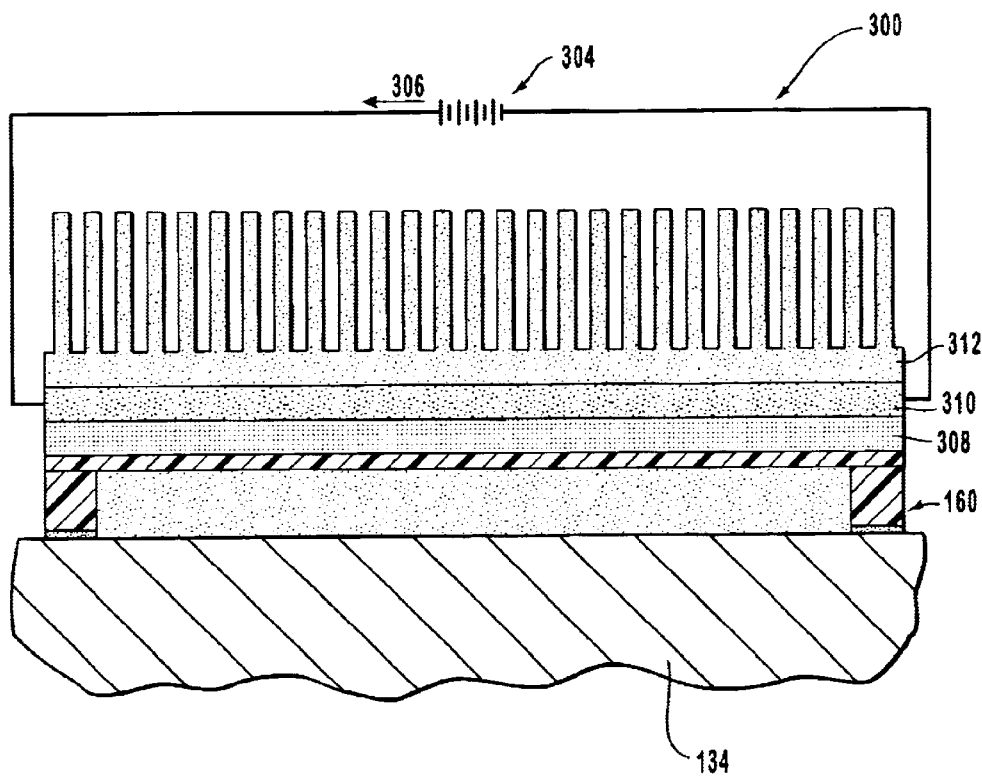
FIG. 23 is a side cross-sectional view of a temperature control apparatus capable of both heating and cooling applied to a DDDS according to the present invention.
Figure 24:
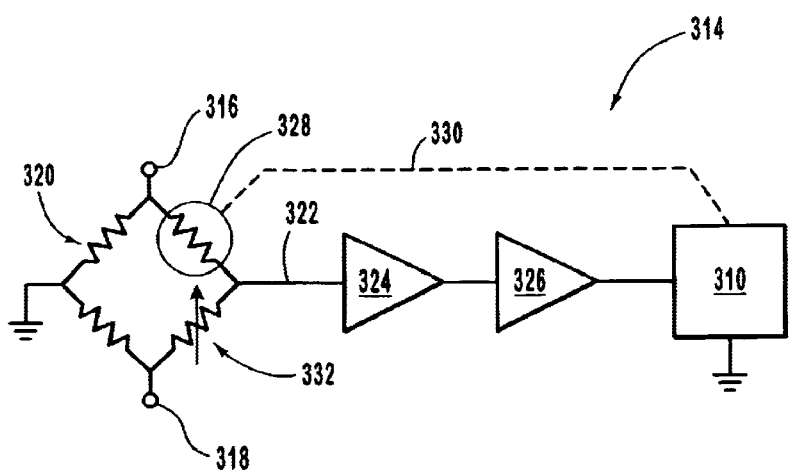
FIG. 24 is a schematic for a closed loop temperature controller for the temperature control apparatus of FIG. 23 according to the present invention.

An example of using the embodiment of the present invention illustrated in FIGS. 23–24 comprises using a temperature control apparatus 300 which is capable of heating and cooling, such that the rate of absorption of a drug formulation in a DDDS can be increased or decreased, as needed.

For example, as shown in FIG. 23, if the level of the drug in the patient's system requires adjusting, the temperature control apparatus 300 is placed on a DDDS 160. Heating will result in an increase in drug absorption (as previously discussed) and cooling will reduce drug absorption to prevent overdose. FIG. 23 illustrates the temperature control apparatus 300 as a thermoelectric module which is be used for both heating or cooling. The temperature control apparatus 300 functions as a small heat pump, wherein a low voltage DC power source 304 provides a current in one direction 306 to a thermoelectric unit 310 which results in heating on a first side 308 (preferably a ceramic substrate) of the temperature control apparatus 300 and cooling on a second side 312 (preferably a finned dissipation structure) of the temperature control apparatus 300. If the current direction is reversed, the first side 308 will cool and the second side will heat.

The temperature control apparatus 300 may be control with a closed loop temperature controller 314, as shown in FIG. 24. The temperature controller 314 comprises a positive DC node 316 and a negative DC node 318 supplying circuit to a primary circuit 320. The primary circuit 320 delivers an electrical signal 322 through a voltage amplifier 324 and a power amplifier 326 to the thermoelectric unit 310. The primary circuit 320 further includes a temperature sensor 328 receiving a temperature signal 330 from the thermoelectric unit 310, and further includes a temperature adjustment mechanism 332, which adjusts the electrical signal 322.

A variety of drugs and drug classes can be utilized with such treatments. The drugs include, but are not limited to, nicotine, nitroglycerin, clonidine, dexamethasone, fentanyl, sufentanil, and insulin. The drug classes include, but are not limited to, androgen, non-steroidal anti-inflammatory agents, anti-hypertensive agents, analgesic agents, anti-depressants, anti-cancer agents, anti-diabetic agents, steroids, anti-migraine agents, anti-asthma agents, and agents for smoking cessation.

It is, of course, understood that the heating devices discussed above could be replaced by an infrared heating device with a feedback mechanism. All of the controls and variations in controls discussed above would apply to such an infrared heating device. The advantage of infrared radiation over simple heat is that the former, with proper wavelengths, penetrates deeper into a patient's skin.

Another aspect of the present invention is to use heat and other physical means, such as ultrasound, microwave, electric current, and vibration, to improve absorption of drugs from depot/storage sites. Such depot/storage sites may exist as a result of a drug administered from a dermal patch or a drug directly injected or implanted under the skin surface.

The kind of formulations that may respond to the physical inducing means discussed above are:

Ultrasound: particles containing drug formulation that can break down in size when treated with ultrasound.

Microwave: drugs that have limited solubility in surrounding body fluid, but the solubility increases significantly with increasing temperature; and solid formulations whose erosion/degradation speed can be significantly increased by increasing flow/exchange of body fluid surrounding it.

Electricity: drugs that exist in ionized form in the formulations and/or surrounding body fluid.

Vibration: drugs that have limited solubility in body fluid; solid formulations whose erosion/degradation speed can be significantly increased by increasing flow/exchange of body fluid surrounding it.

EXAMPLE 15

Figure 25:
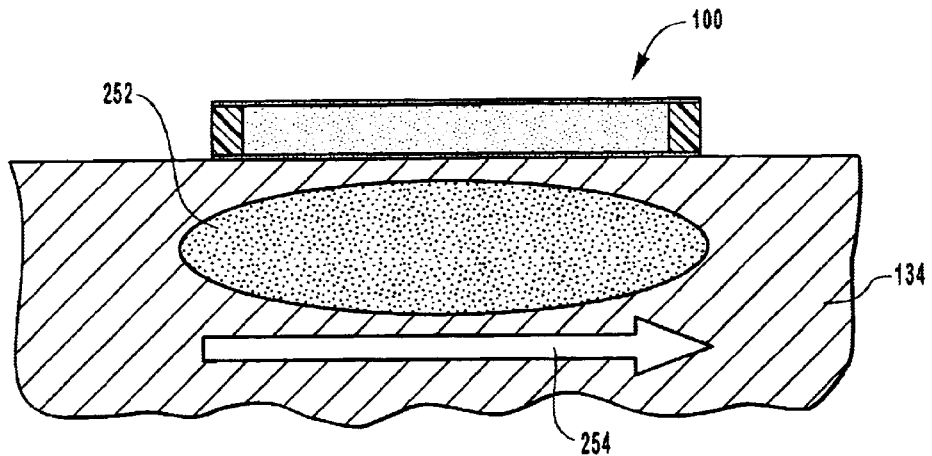
FIG. 25 is a side cross-sectional view of a temperature control apparatus applied directly to a patient's skin according to the present invention.

One example of enhanced depot site absorption using the embodiment of the present invention illustrated in FIGS. 1 and 2 for administering analgesic material for pain relief consists of a patient or care giver placing the DDDS, such as a 5 fentanyl-containing DDDS, on the skin of the patient at a first location. After sufficient depletion of the drug in the DDDS, the DDDS is removed and a second DDDS is placed on the skin of the patient at a second location to continue drug delivery. If an episode of breakthrough pain occurs, the temperature control apparatus 100 can be applied directly to the patient's skin 134 at the first location (the DDDS is no longer present), as shown in FIG. 25. The heat from the temperature control device 100 increases the speed of drug release from the depot site 252 in the first skin site and the tissues thereunder to give an increased drug absorption into the systemic circulation 254 to treat the breakthrough pain.

EXAMPLE 16

An example of storage site absorption using the embodiment of the present invention illustrated in FIGS. 1 and 2 consists of a patient or care giver introducing an extended release insulin into his skin by injection or other method such as ultrasound speed hitting (such as products similar to those developed by Powdedject Pharmaceutical, United Kingdom). In the extended release insulin formulation, most of the insulin molecules are in crystalline form. After injection, insulin is released from the crystalline from slowly as the crystals slowly dissolve in the surrounding body fluid. This provides a baseline insulin release into the systemic circulation. However, the patient needs additional insulin above the baseline release to suppress sugar from meals. Thus, before each meal the patient places a temperature control apparatus 100, preferably designed to control heat for a predetermined time (i.e., between about 15 and 60 minutes), onto the skin over the injection site where the injected extended release insulin formulation resides. The heat from the temperature control apparatus 100 increases flow of the blood and another body fluid in the tissues surrounding the extended insulin formulation, which increases the dissolution speed of the insulin and carries the insulin into the systemic circulation at higher rate. The heating duration of the temperature control device 100 is, preferably, designed to last just long enough to release the adequate amount of extra insulin to deal with the sugar from the meal. Thus, the patient receives proper insulin absorption adjustment from the extended release formulation, and does not have to make a choice between taking additional insulin shots before meals or suffer the physiological consequences caused by high blood sugar from the meals.

EXAMPLE 17

Another example of storage site absorption using the embodiment of the present invention illustrated in FIGS. 1 and 2 consists of a patient or care giver injecting a drug mixed in controlled release particles under the skin surface. By way of example, a controlled release formulation of analgesics may comprise an analgesic, such as sufentanil, alfentanil, remifentanil, and morphine, which is incorporated into a controlled release drug delivery system (such as Atrigel™ by Atrix Laboratories, Inc., Fort Collins, Colo., USA) comprising a biodegradable, biocompatible polymer (s) [i.e., poly(DL-lactide), poly(DL-lactide-co-glycolide), poly(DL-lactide-co-ε-caprolactone), polycaprolactone, or a combination thereof] in a biodegradable solvent (i.e., N-methyl-2-pyrrolidone). The controlled release formulation is generally injected into a patient within 3 cm, preferably within 1 cm, and most preferably 0.3 cm, from the skin to control his cancer pain.

It is understood that any homopolymer or copolymer of lactic and glycolic acid can be utilized. The lactic/glycolic acid polymers are solids, wherein the drug and polymers are both dissolved in a biodegradable solvent. After the injection, the biodegradable solvent diffuses out leaving behind the polymer(s) in the form of precipitated, biodegradable particles, which holds most of the sufentanil. As the polymer particles gradually erodes/degrades, the sufentanil is released into the systemic circulation to treat the cancer pain. The release rate of sufentanil is S determined by how quickly the polymer particles erodes/degrades in the body.

The active drug may also be incorporated and delivered into the storage site using different methods, such as mixing the drug with the biodegradable, biocompatible polymer(s) in a solvent, evaporating the solvent to obtain polymer particles mixed with the active drug. The size of the drug containing polymer particles should be, small enough to be incorporated (not dissolved) into a suspension in a liquid (preferably an aqueous liquid). The suspension is injected into the patient's tissue proximate the skin surface. The liquid quickly leaves the depot site, leaving behind a polymer implant containing the active drug. The release of active drug from the polymer implant can be increased in the manner described above.

Regardless of the implantation method, the normal release rate of sufentanil is usually sufficient to treat the patients baseline cancer pain, but not enough to treat breakthrough pain. When the patient feels a breakthrough pain is coming, he places a temperature control apparatus 100 over the skin site under which the formulation was injected. The increased blood/body fluid flow caused by the heat increases the erosion/degradation speed of the polymer particles and hence the speed of release of sufentanil. When the breakthrough pain is over, the patient stops the heating (such as by removing the heating patch or covering the holes 114 on the top wall 104—see FIG. 2) and the polymer particle erosion/degradation speed gradually returns to normal which returns the sufentanil release rate back to a normal, pre-heated rate.

EXAMPLE 18

The effects of heating on the release of a drug incorporated in a biocompatible, biodegradable polymer matrix were examined. An anesthetic (i.e., lidocaine) was incorporated into the polymer matrix (i.e., lactide/glycolide polymer) to form an anesthetic drug/polymer composition. The anesthetic drug/polymer composition may be used for injecting/planting under the skin of a patient, wherein the drug is gradually released into the body as the polymer matrix slowly erodes in the body.

The anesthetic drug/polymer composition was made by dissolving one tenth of one gram of lactide/glycolide polymer (Medisorb Grade 8515DL, Medisorb Technologies International, L.P., Cincinnati, Ohio, USA) and 0.1 gram of lidocaine base in 2 grams of acetone to form a solution. Approximately 5 mL of water (pH adjusted to above 8) was slowly added into the solution while the solution was stirred by a rapidly rotating Teflon coated magnetic bar. A Medisorb-lidocaine mixture precipitated out as a textured material attached on the magnetic bar and as fine particles suspended in the solution. Approximately 0.5 mL of the solution containing the fine particles were injected into a 0.2 micrometer PTFE filter (Nalgene, 25 mm). Normal saline was infused through the filter via a 3M™ 3000 Modular Infusion Pump at a rate of 2 ml/hr for approximately 7 days. This was to wash away the lidocaine that was not incorporated in to the Medisorb matrix and particles smaller than 0.2 micrometer, while lidocaine-polymer particles bigger than 0.2 micrometer were trapped in the filter. The particles slowly degraded due to hydrolysis and thus gradually releases licocaine to the saline passing through the filter.

A blunt needle was tightly attached to the exit end of the filter, and a thin plastic tube was attached to the blunt needle. Filtered solution from the distal end of the thin plastic tube was collected according the following steps:

Step 1: Filter at room temperature (about 24° C.) and collect the filtered solution into a glass vial for approximately 1 hour.

Step 2: Immerse the filter into a 36° C. (approximate) water bath, wait approximately 1 hour, and collect the filtered solution from the thin tube for approximately 1 hour.

Step 3: Increase the temperature of the water bath to about 44° C., wait approximately 1 hour, and collect the filtered solution for approximately 1 hour.

Step 4: Take the filter out of the water bath and leave at room temperature (about 24° C.) for approximately 0.5 hours, collect the filter solution for approximately 1 hour.

Step 5: Repeat Step 4 after approximately 2 hours.

Saline was infused through the filter at the 2 mL/hour rate for the entire experiment. The solution coming out of the thin plastic tub during non-collecting time were discarded. Concentrations of lidocaine in above collected solutions were determined by an HPLC (High Performance Liquid Chromatography) method.

Lidocaine release rates from the polymer matrix at different temperatures were calculated from lidocaine concen trations in the collected samples. The release rates are shown in Table E, as follows:

TABLE E

| Step | Temperature | Lidocaine Release Rate (mcg/hour) |
|---|---|---|
| 1 | 24° C. | 0.36 |
| 2 | 36° C. | 0.61 |
| 3 | 44° C. | 1.59 |
| 4 | 24° C. | 0.47 |
| 5 | 24° C. | 0.38 |

As the results demonstrate, the lidocaine release rate increased when temperature at the filter (and hence the temperature of the lidocaine-polymer particles) was increased, and decreased when the temperature was decreased. Although the filter temperature in Steps 4 and 5were the same, the lidocaine release rate in Step 5 was lower than that in Step 4, and approaches that in Step 1.

Although the total quantities of Medisorb and lidocaine in the filter were not measured, the relative differences in the lidocaine release rates at different temperatures demonstrate that lidocaine release rate from Medisorb polymer increases with temperature. The finding that lidocaine release rate in Step 5 was lower than that in Step 4 suggest that the release rate decreases gradually after the temperature is lowered.

Since the degradation (hydrolysis) of Medisorb polymer is believed to control the release rates, these results suggest that Medisorb polymer degradation rate increases with increasing temperature. This suggests that the release rate of any drug incorporated in the Medisorb matrix (or other similar materials) and injected into the body can be increased by increasing temperature. In addition to increasing hydrolysis rate of the Medisorb-lidocaine particles, heat is also expected to increase the flow of body fluid surrounding the particles in the storage site in actual application, which should cause an additional increase in the drug absorption rate.

Another experiment was conducted on the Medisorb (same type as discussed above). A first sample of the Medisorb (transparent beads) weighing 0.1024 grams was placed in a first glass vial with 9.9024 grams of 0.9% sodium chloride injection solution. The first glass vial was sealed with parafilm and placed in an oven which maintained a temperature of about 43° C. A second sample of the Medisorb weighing 0.1028 grams was placed in a second glass vial with 9.9167 grams of 0.9% sodium chloride injection solution. The second glass vial was sealed with parafilm and placed in a room with a temperature of about 23° C.

After 29 days, few visible change had occurred to the Medisorb held at room temperature (second sample). However, the Medisorb held at about 43° C. changed from a transparent material to a milky-white color with smoothed edges. The Medisorb beads also appeared smaller than the original size. This simple experiment demonstrates that the degradation rate of the Medisorb polymer increases with increasing temperature.

EXAMPLE 19

Still another example of storage site absorption using the embodiment of the present invention illustrated in FIGS. 1 and 2 consists of a patient or care giver implanting a solid piece (i.e., plate, rod, or the like) made of a biocompatible, bioerodable material(s), such as listed in Example 16, under the skin surface. By way of example, insulin can be incorporated into such a material. The insulin-containing solid piece is implanted into a diabetic patient in a position within 3 cm, preferably within 1 cm, and most preferably within 0.3 cm, from the skin. The insulin release rate from the solid piece is designed to be sufficient to provide the baseline insulin need for extended period of time (e.g., a few months). Before each meal, the patient places the temperature control apparatus 100, preferably with a pre-determined heating duration, on to the skin site under which the solid piece resides. The heat from the temperature control apparatus 100 increases the flow of blood or other body fluid surrounding the solid piece, thus increases the erosion/degradation of the solid piece and delivers extra insulin to the systemic circulation to suppress the sugar from the meals. After the pre-determined duration of temperature control apparatus 100 is over or after the patient discontinues the heating from the temperature control apparatus 100, the erosion/degradation rate of the solid piece gradually returns to normal, as does the insulin release rate.

Furthermore, such a system can be used with testosterone in a solid piece which implanted in the patient's skin. Preferably, the temperature control apparatus 100 is designed to last substantially longer (i.e., approximately 6–10 hours). The patent applies the temperature control apparatus 100 on the skin site under which the solid piece resides to obtain increased testosterone levels in the blood in the period from morning to evening when testosterone is most needed.

Although only a small number of drugs have been disclosed in Examples 13–18, any drug used in a treatment that fits the following description may potentially benefit from the methods: 1) the treatment requires that the drug have a baseline deliver rate over long treatment duration (such as longer than a day, preferably over a week), and 2) the treatment requires the drug to have increased delivery rates for a period or periods of time during the long treatment duration. A variety of drugs and drug classes can be utilized with such treatments. The drugs include, but are not limited to, nicotine, testosterone, estradiol, nitroglycerin, clonidine, dexamethasone, tetracaine, lidocaine, fentanyl, sufentanil, progestrone, insulin, prilocaine, bupivacaine, sumatriptan, and dihydroergotamine. The drug classes include, but are not limited to, androgen, estrogen, non-steroidal anti-inflammatory agents, anti-hypertensive agents, analgesic agents, anti-depressants, antibiotics, anti-cancer agents, local anesthetics, antiemetics, anti-infectants, contraceptives, anti-diabetic agents, steroids, anti-allergy agents, anti-migraine agents, agents for smoking cessation, anti-asthma agents, and anti-obesity agents.

EXAMPLE 20

Still yet another example of storage site absorption using the embodiment of the present invention illustrated in FIGS. 1 and 2 consists of a patient or care giver imbedding a drug into the depot site. By way of example, a care giver can embed an anti-migraine drug, such as a powder form of dihydroergotamine, sumatriptan, or ergotamine, by hitting the drug into a depot site under the skin at high speed (such as by a device manufactured by Powderject Pharmaceutical, United Kingdom) when a patient feels an episode of migraine headache is imminent. With the Powderject device, the drug powder is accelerated to a speed higher than the speed of sound and hit into the skin. A temperature control apparatus 100, preferably lasting approximately 1 hour, is immediately applied on the skin over the location of the embedded drug. The heat from the temperature control apparatus 100 increases the speed of the body fluid flow surrounding the anti-migraine drug and carries the anti-migraine drug into the systemic circulation faster. As a result, therapeutical blood concentrations of the anti-migraine drug is reached earlier and in time to treat the migraine headache.

This technique may also be used to deliver a preventative baseline release rate of a drug, such as anti-migraine drug or nitroglycerine. A heating patch is then applied to release extra drug when a medical episode begins.

It is, of course, understood that the heating devices discussed above could be replaced by an infrared heating device or a microwave heating device with a feedback mechanism. All the controls and variations in controls discussed above would apply to such devices.

EXAMPLE 21

Ultrasound can be used to increase release rate of injected controlled release drug formulations, particularly, when the controlled release formulations are in the form of relatively large particles (i.e., 25 µm or larger). The controlled release formulation is injected into the patient's tissues within 3 cm, preferably within 1 cm, and most preferably 0.3 cm from the skin. The erosion/degradation rate of the particles determines the rate of release of the drug, and the steady state release rate of the drug is designed to deliver a therapeutical level of drug to the patient. For analgesic drugs, the steady state release rate is usually slightly below that needed to treat an average person's post-operative pain. For a particular patient in whom the steady state release rate is not sufficient (because of his pharmacokinetics and/or level of pain), an ultrasound is directed into formulation and breaks the particles into smaller ones (this requires that the particles are capable of being broken by ultrasound).

This increases the surface area of the formulation exposed to the surrounding body fluid, and hence increases the release rate for the rest of the administration. This method allows the administration of a low release rate formulation which is safe, and then increasing the release rate for patients who need higher delivery rates. The intensity, frequencies, and duration of ultrasound can be chosen to increase the release rate to proper levels. Exemplary ultrasound treatment and devices can be found in U.S. Pat. No. 4,948,587 issued Aug. 14, 1998 to Kost et al., hereby incorporate herein by reference.

EXAMPLE 22

Figure 26:
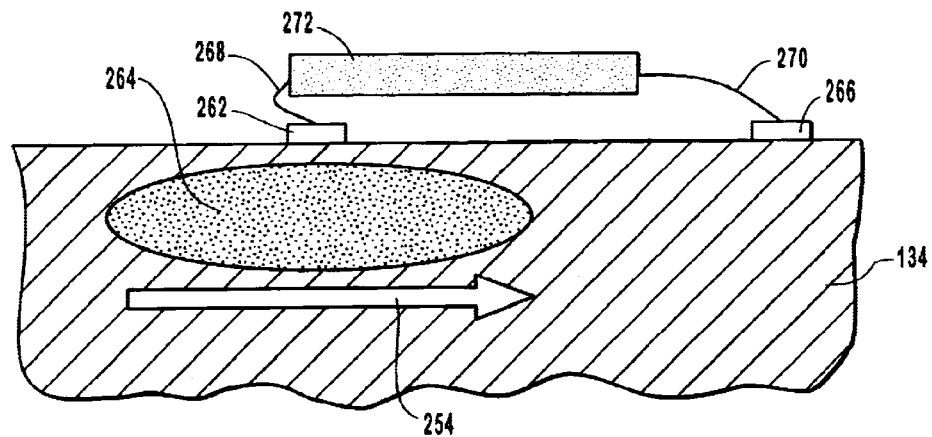
FIG. 26 is a side cross-sectional view an electrical mechanism for increasing drug absorption according to the present invention.

The generation of an electric potential on a portion of a patient's body can be used to increase release rate of injected controlled release drug formulations, particularly, when the controlled release formulations exist in ionized form in the formulations and/or surrounding body fluid. For example, when a controlled release insulin is injected into a diabetic patient's skin, the normal release rate of insulin from this formulation is controlled by the dissolution rate of the particles in which insulin resides wherein the normal release rate provides an adequate baseline insulin level in the patient. As shown in FIG. 26, the patient places a first electrode 262 on the skin 134 over the injection site of the controlled release insulin formulation 264. A second electrode 266 is placed on a skin 134 in a position near the injection site of the controlled release insulin formulation 264 (i.e., at least a few centimeters away). Before each meal when the patient needs to increase his blood insulin level to suppress sugar from the meal, the patient connects the first electrode 262 and the second electrode 266 with wires 268 and 270, respectively, to an electric current generating device 272. The electric current generating device 272 introduces an electrical potential between the first electrode 262 and the second electrode 266. Preferably, with the use of insulin, the electrical amperage should be in the range of between about 0.2 and 4 mA. Because at the physiological pH, insulin molecules carry net negative electric charges, the first electrode 262 should have a negative charge which pushes the negatively charged insulin away from the body fluid surrounding the formulation and into the systemic circulation 254. This makes the insulin release faster. Preferably, the intensity and duration of the current can be altered with the electric current generating device 272 to deliver the requisite therapeutic amount of extra insulin.

EXAMPLE 23

Figure 27:
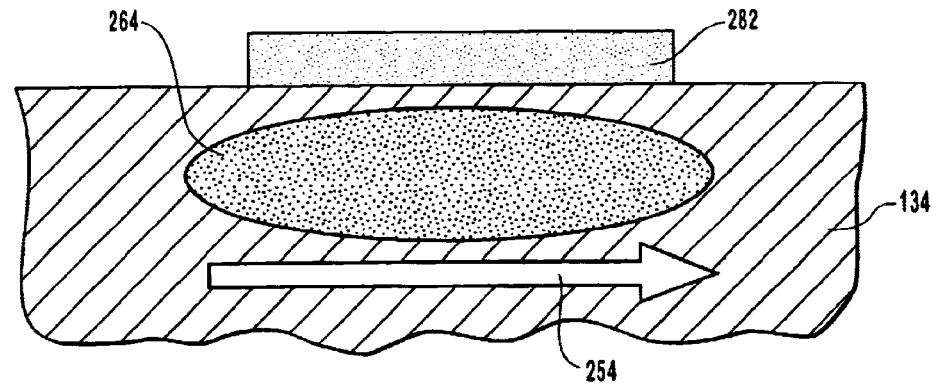
FIG. 27 is a side cross-sectional view a vibrational mechanism for increasing drug absorption according to the present invention.

The generation of a vibration over the injection site of controlled release drug formulations can be used to increase release rate of the formulations, particularly, when the controlled release formulations have limited solubility in body fluid or with solid formulations whose erosion/degradation speed can be significantly increased by increasing flow/exchange of body fluid surrounding the solid formulation. For example, when a controlled release insulin is injected into a diabetic patient's skin, the normal release rate of insulin from this formulation is controlled by the erosion/degradation or dissolution rate of the particles in which insulin resides wherein the normal release rate provides an adequate baseline insulin level in the patient. As shown in FIG. 27, before each meal, the patient places a vibration generating device 282 on the skin 134 over the injection site of the controlled release insulin formulation 264. The vibration generating device 282, preferably, delivers vibration of between about 20 and 400 Hz. The vibration agitates the body fluid (not shown) surrounding the controlled release insulin 264 and increases its circulation. As a result, more insulin is released from the controlled release insulin formulation 264 to the systemic circulation 254 shortly before the meal to suppress the sugar from the meal. Preferably, the intensity and duration of the vibration can be altered with the vibration generating device 282 to deliver the requisite therapeutic amount of extra insulin.

Although only a few drugs have been disclosed in Examples 19–22, any drug used in a treatment that fits the following description may potentially benefit from the physical methods for inducing increased release: 1) the treatment requires that the drug have a baseline deliver rate over long treatment duration (such as longer than a day, preferably over a week), 2) the treatment requires the drug to have increased delivery rates for a period or periods of time during the long treatment duration, and 3) the formulations respond to the one or more of the physical methods for inducing increased release. A variety of drugs and drug classes can be utilized with such treatments. The drugs include, but are not limited to, nicotine, testosterone, estradiol, nitroglycerin, clonidine, dexamethasone, tetracaine, lidocaine, fentanyl, sufentanil, progestrone, insulin, prilocaine, bupivacaine, sumatriptan, and dihydroergotamine. The drug classes include, but are not limited to, androgen, estrogen, non-steroidal anti-inflammatory agents, anti-hypertensive agents, analgesic agents, anti-depressants, antibiotics, anti-cancer agents, local anesthetics, antiemetics, anti-infectants, contraceptives, anti-diabetic agents, steroids, anti-allergy agents, anti-migraine agents, and agents for smoking cessation.

EXAMPLE 24

Another example of the present invention comprises using a temperature control apparatus 300, similar to that shown in FIG. 23, which is capable of heating and cooling, such that the rate of absorption of injected controlled release drug formulation can be increased or decreased, as needed.

Figure 28:
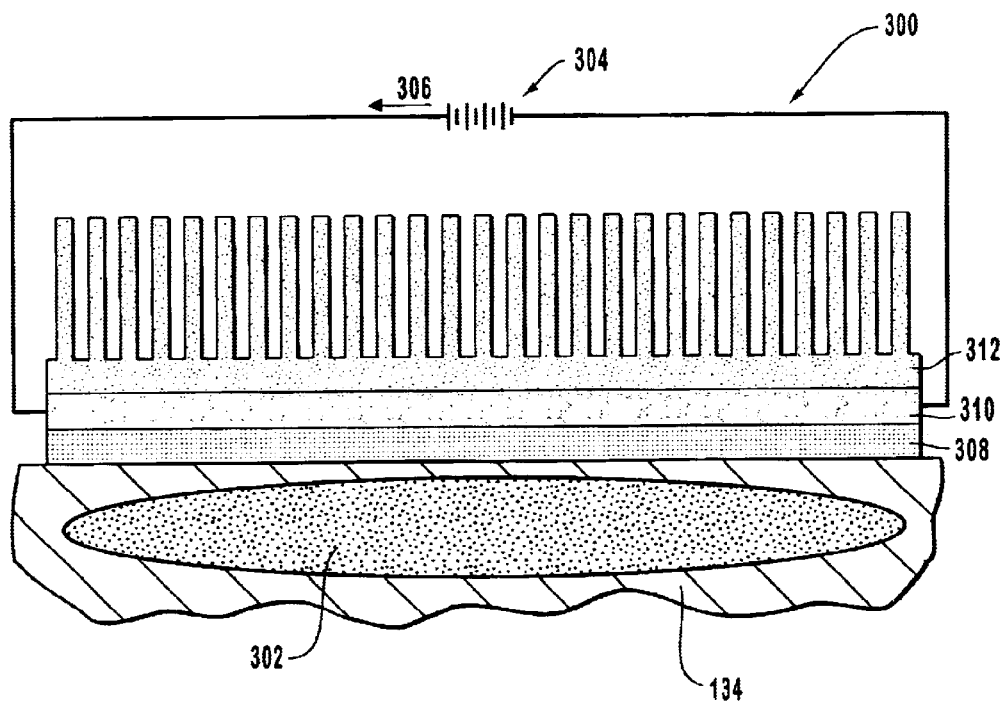
FIG. 28 is a side cross-sectional view of a temperature control apparatus capable of both heating and cooling applied directly to a patient's skin according to the present invention.

For example, when a controlled release drug formulation is injected into a patient's skin, the normal release rate of the drug from this formulation is controlled by the erosion/degradation rate of the particles in which the drug resides wherein the normal release rate provides an adequate baseline drug level in the patient. As shown in FIG. 28, if the level of the drug in the patient's system requires adjusting, the temperature control apparatus 300 is placed on the skin 134 over the injection site of the controlled release drug formulation 302. Heating will result in an increase in drug absorption (as previously discussed) and cooling will reduce drug absorption to prevent overdose. FIG. 23 illustrates the temperature control apparatus 300 as a thermoelectric module which is be used for both heating or cooling. The temperature control apparatus 300 functions as a small heat pump, wherein a low voltage DC power source 304 provides a current in one direction 306 to a thermoelectric unit 310 which results in heating on a first side 308 (preferably a ceramic substrace) of the temperature control apparatus 300 and cooling on a second side 312 (preferably a finned dissipation structure) of the temperature control apparatus 300. If the current direction is reversed, the first side 308 will cool and the second side will heat. The temperature control apparatus 300 may be control with a closed loop temperature controller, as shown previously in FIG. 24.

A variety of drugs and drug classes can be utilized with such treatments. The drugs include, but are not limited to, nicotine, nitroglycerin, clonidine, dexamethasone, fentanyl, sufentanil, and insulin. The drug classes include, but are not limited to, androgen, non-steroidal anti-inflammatory agents, anti-hypertensive agents, analgesic agents, anti-depressants, anti-cancer agents, anti-diabetic agents, steroids, anti-migraine agents, and agents for smoking cessation.

EXAMPLE 25

Another example of the present invention comprises using the temperature control apparatus 300, as shown in FIG. 23, or any device which is capable of cooling the skin in conjunction with an injectable liquid drug delivery formulation containing thermal gel.

The main difference between a thermal gel and a regular gel is that a thermal gel is a liquid in room temperature (i.e., about 20–25° C.) and is a gel at body temperature (i.e., about 37° C.), whereas, with regular gel, the viscosity of the gel generally lowers with increasing temperature. Thus, while the thermal gel is at room temperature (i.e., in liquid form), a drug formulation is mixed into the thermal gel. The thermal gel/drug mixture may then be easily drawn into a syringe and injected to the patient. Once in the patient's body, the thermal gel/drug mixture quickly solidifies into a gel. The gel then dissolves over time releasing the drug formulation into the patient systemic circulation.

Using a cooling device, such as the temperature control apparatus shown in FIG. 23, the thermal gel/drug mixture which has solidified under the skin can be cooled to revert the gel back into a liquid. In a liquid state, the drug formulation diffusion rate and release rate increase, thereby increasing the drug formulation present in the patient's systemic circulation when needed.

An example of a thermal gel is Smart Hydrogel™ developed by Gel Science/GelMed and consists of an entangled network of two randomly grafted polymers. One polymer is poly(acrylic acid) which is bioadhesive and pH-responsive. The other polymer is a triblock copolymer containing poly(propylene oxide) ("PPO") and poly(ethylene oxide) ("PEO") segments in the sequence PEO-PPO-PEO.

An example of using the present invention with a thermal gel is the delivery of additional insulin to a diabetic patient prior to the intake of food. The thermal gel containing the insulin can be injected subcutaneously in order to form a gel to release a continuous baseline dosage of insulin. At a meal when insulin is needed to absorb extra sugar in the circulation, the patient can apply the cooling device on the skin adjacent the injection site and cool the injection site to a temperature below the gelling temperature of the thermal gel/insulin mixture. The gel will, of course, become a liquid and increase the insulin level in the patient's body to compensated for the ingested meal. This process can be repeated many times until the injected thermal gel/insulin mixture is gone. The advantage of this drug delivery system is that the diabetic patient can control insulin delivery during the course of a few days, even a few weeks, with only one injection.

EXAMPLE 26

Figure 29:
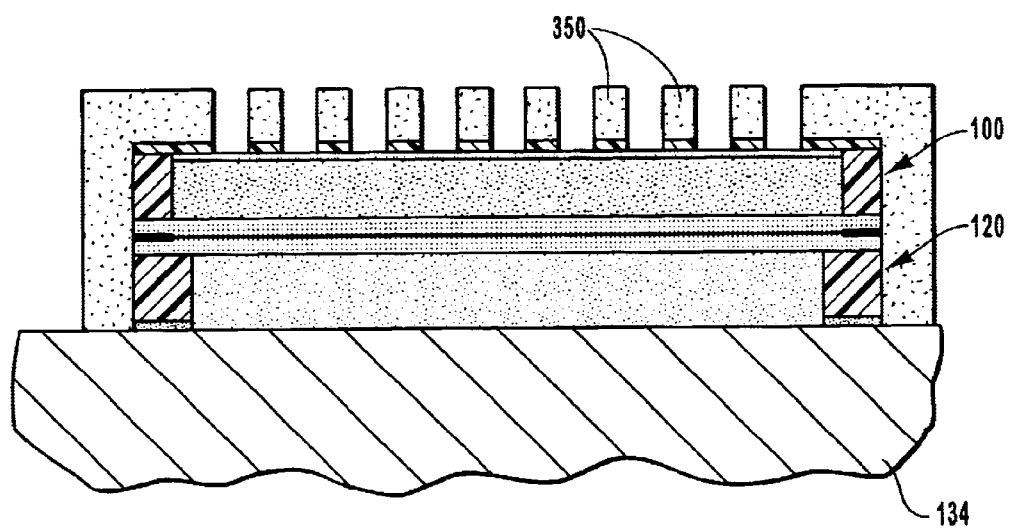
FIGS. 29–32 is a side cross-sectional view an insulative material over a DDDS and injected or depot drug sites for minimizing temperature variation and/or increasing the temperature of the DDDS and the skin thereunder according to the present invention.

As shown in FIG. 29, an insulating material can be incorporated with the controlled temperature apparatus to assist in not only minimizing the temperature variation, but also increasing the temperature of the DDDS and the skin under it (by decreasing heat loss), each of which tend to increase dermal drug absorption.

FIG. 29 illustrates a configuration similar to that illustrated in FIG. 4 wherein the temperature control apparatus 100 of FIG. 2 is attached to the DDDS 120 of FIG. 3. The DDDS 120 attached to a portion of the skin 134 of a patient. An insulating sleeve 350 abuts the skin 134 and encases a substantial portion of the temperature control apparatus 100 and the DDDS 120.

Figure 30:
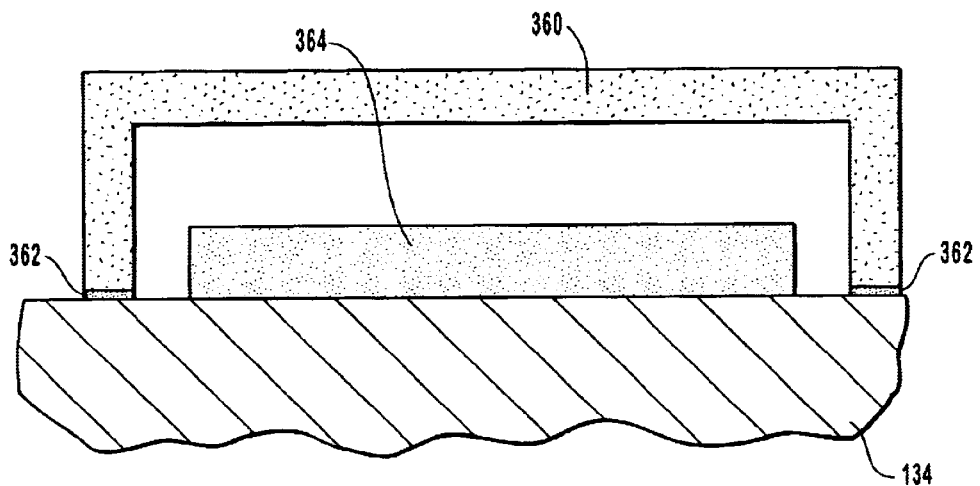
Figure 31:
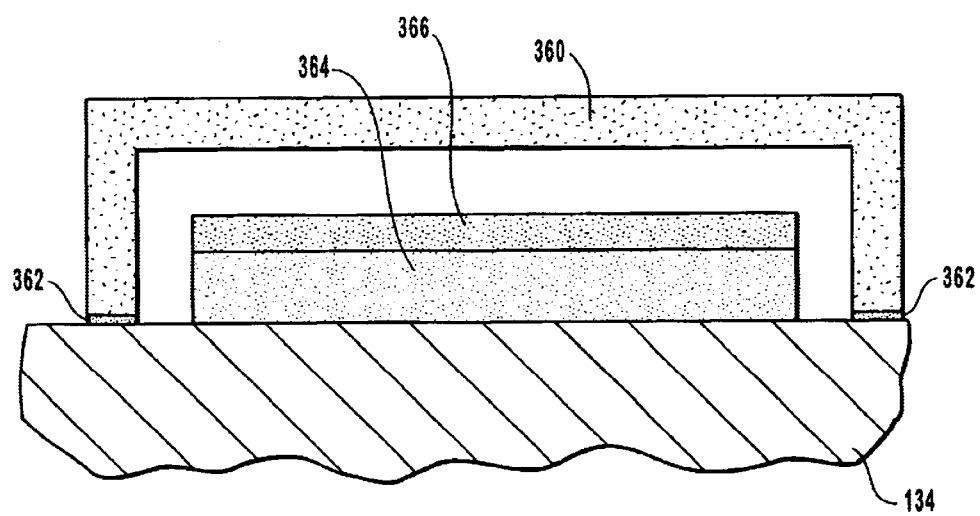
Figure 32:
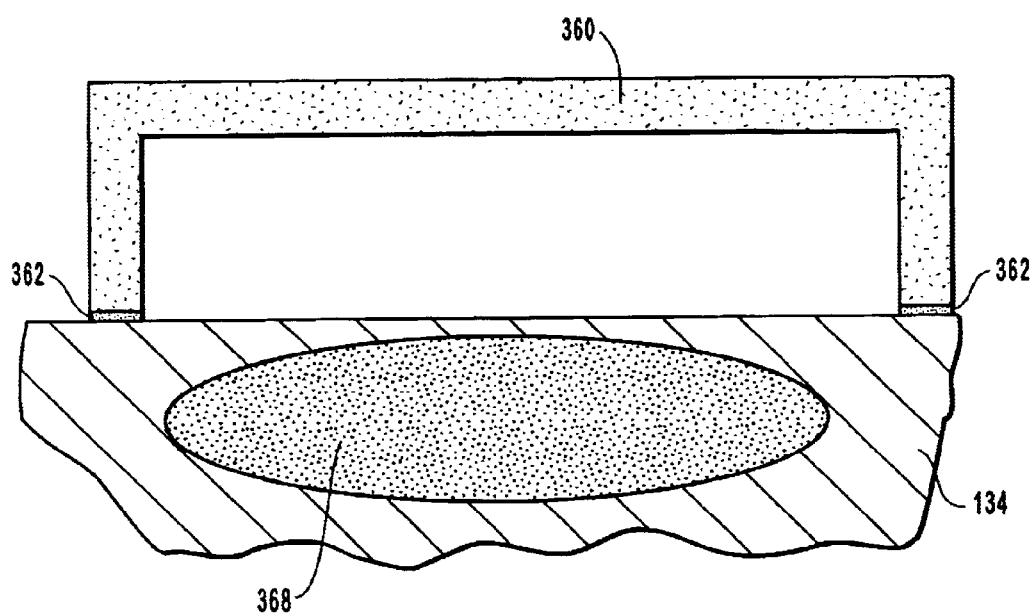

FIG. 30 illustrates another insulating sleeve 360 made of an insulating material, such as closed-cell foam tape, with adhesive edges 362 attached to a patient's skin 134, slightly larger than and covering a DDDS 364. FIG. 31 illustrates the insulating sleeve 360 covering a heating apparatus 366 and the DDDS 364 attached to a patient's skin 134. FIG. 32 illustrates the insulating sleeve 360 covering an area over the skin 134 where an injected/implanted/controlled/extended release drug formulation 368 has been located.

EXAMPLE 27

Another application of the present invention involves the use of a heating device, such as discussed above, in conjunction with a typical liquid drug injection. For some drugs, increased speed of absorption into the systemic circulation after they are injected into the body may provide treatment to the patients. For instance, to be effective, the anti-migraine drug, dihydroergotamine, must reach an effective concentration level in the blood stream within a certain amount of time from the onset of the migraine attack or the drug will be ineffective. Currently, a drug's absorption into the patient's systemic circulation cannot be altered after it is injected. Thus, the controlled heating aspect of the present invention can be used to increase the absorption speed of subcutaneously and intramuscularly injected drugs.

For example, after a drug is injected subcutaneously or intramuscularly, a heating patch, such as described in the above examples, may be placed on the skin under which the injected drug resides. The heating increases the circulation of body fluid surrounding the injected drug, increases the permeability of blood vessel walls in the surrounding tissue, and, thus, results in increased speed of absorption of the drug into the systemic circulation.

Such a method would be useful for drugs which are injected into a part of the body that can be heated by a heating means on or outside the skin and whose effect can be improved by increased absorption speed into the systemic circulation or deeper tissues. Such drugs may include; anti-migraine agents, anti-hypertensive agents, analgesics, antiemetics, cardiovascular agents. Specific drugs may include dihydroergotamine, ergotamine, sumatriptan, rizatriptan, zolmitriptan, and other selective 5-hydroxytryptamine receptor subtype agonists, morphine and other narcotic agents, atropine, nitroglycerin, fentanyl, sufentanil, alfentanil, and meperidine.

Since increased absorption speed into the systemic circulation usually can cause higher peak concentrations in the blood, this technology may also be used to increase peak blood concentrations of drugs that are injected subcutaneously and intramuscularly.

Some drugs need to be injected intravenously because systemic absorption for subcutaneous and intramuscular injections take too long to take effect. However, intravenous injection is more difficult to perform and involves more risks. With the use of the present invention, the absorption speed of some drugs may be increased enough so that subcutaneous or intramuscular injection can provide sufficient speed of absorption. Therefore, this technology may also be used for replacing intravenous injections with subcutaneous or intramuscular injections for some drugs.

As a specific example, a patient may inject himself with sumatriptan or dihydroergotamine subcutaneously after he feels a migraine attack. He then removes a heating patch containing a heat generating medium comprising iron powder, activated carbon, water, sodium chloride, and sawdust (similar to Example 1) out of its air-tight container and places it over the injection site. The heating patch quickly increases the temperature of the skin under the heating patch into a narrow range of 39–43° C. and maintains it there for at least 15 minutes. The circulation speed of the body fluid surrounding the injected drug and the permeability of the blood vessels in the surrounding tissues are both increased by the heating. As a result, the drug enters the systemic circulation and reaches the acting site more rapidly, and the patient receives more rapid and/or better control of the migraine attack.

In another example, a nurse can inject morphine into a patient's muscle tissue to treat severe pain. The nurse then places a heating patch, as describe above, over the injection site. The speed of morphine absorption into the systemic circulation is increased as previously discussed. As a result, the patient receives more rapid and/or better pan control.

EXAMPLE 28

Another application of the present invention involves the use of a heating device, such as discussed above, to mimic circadian patterns. For example, testosterone or its derivatives, such as testosterone enanthate and testosterone cypionate, can be injected intramuscularly into men to substitute or replace diminished or absent natural testicular hormone. Testosterone enanthate and testosterone cypionate are preferred over testosterone, as they have longer duration of action than testosterone. However, it is understood that testosterone or its derivative, such a testosterone ester, may be incorporated into a controlled release polymer matrix, such as homopolymer or copolymer of lactic and glycolic acid, preferably poly(DL-lactide), poly(DL-lactide-co-glycolide), and poly(DL-lactide-co-(-caprolactone)), to increase the duration of action. Following intramuscular injection, testosterone enanthate is absorbed gradually from the lipid tissue phase at the injection site to provide a duration of action of up to 2–4 weeks. However, natural blood testosterone concentrations in healthy man are higher in a day and lower in the night. So blood testosterone concentrations obtained from injected testosterone derivatives do not mimicking the natural circadian pattern.

By way of example, a patient can inject testosterone enanthate either subcutaneously or intramuscularly (if intramuscularly, the injection should be relatively close to the skin surface). The patient then places a heating patch on the injection site every morning (until all the injected testosterone enanthate is depleted). The heating patch quickly increases the temperature of the injection site to a narrow range, and maintains it therefore a desirable duration of time (i.e., about 8 hours). They heating causes increased release of testosterone enanthate and/or increased rate of conversion from testosterone enanthate to testosterone, and, thus, higher blood testosterone concentrations. The "used-up" patch is removed before a new heating patch is placed on the same. Using this intermittent heat application technique, blood testosterone concentrations are low in the night and high in the day, thus mimicking the natural circadian pattern.

Having thus described in detail preferred embodiments of the present invention, it is to be understood that the invention defined by the appended claims is not to be limited by particular details set forth in the above description as many apparent variations thereof are possible without departing from the spirit or scope thereof.

What is claimed is:

1. A controlled heat generating apparatus configured to selectively provide heat in a desired, narrow temperature range for a desired length of time, the apparatus comprising:
   a heating unit capable of generating heat when supplied with electricity wherein said heating unit includes a temperature feedback system; and
   a substantially two-dimensional surface coupled to said heating unit and configured to pass said heat to at least one of:
   (i) a dermal drug delivery system; and
   (ii) a patient's skin.

2. The controlled heat generating apparatus of claim 1, wherein said dermal drug delivery system is in contact with said patient's skin.

3. The controlled heat generating apparatus of claim 1, wherein said substantially two-dimensional surface is configured to pass heat when said surface is in contact with an area of said patient's skin and said skin was previously in contact with said dermal drug delivery system.

4. The controlled heat generating apparatus of claim 1, wherein said substantially two-dimensional surface is configured to pass heat when said surface is in contact with an area of said patient's skin under which a storage site exists.

5. The controlled heat generating apparatus of claim 1, wherein said substantially two-dimensional surface is configured to pass said heat to a rate limiting membrane and a pharmaceutical formulation dispersed within said dermal drug delivery system.

6. The controlled heat generating apparatus of claim 1, wherein said temperature range is a range below 60° centigrade.

7. The controlled heat generating apparatus of claim 1, wherein said desired length of time is between about 3 minutes and about 7 days.

8. The controlled heat generating apparatus of claim 1, further comprising a temperature sensor coupled to said temperature feedback system.

9. The controlled heat generating apparatus of claim 8, wherein said sensor is configured to be selectively coupled to at least one of:
 (i) said dermal drug delivery system; and
 (ii) said patient's skin.

10. In a system that includes a dermal drug delivery system and a heating unit configured to generate heat when supplied with electricity, a method for improving an administration of a pharmaceutical formulation through a patient's skin, the method comprising the steps for:
 using the electrical heating unit to selectively generate heat;
 using a two-dimensional surface of the electrical heating unit to pass the heat to a receiving surface; and
 employing a temperature feedback system to regulate an amount of heat passed to the receiving surface 11. The method of claim 10, wherein the receiving surface comprises at least one of:
 (i) the dermal drug delivery system; and
 (ii) a patient's skin.

12. The method of claim 11, wherein the step for employing a temperature feedback system includes the step for using a temperature sensor to monitor a temperature at the receiving surface.

13. The method of claim 12, wherein the step for employing a temperature feedback system includes the step for transmitting a signal based on the temperature monitored to a controller that regulates an amount of heat generated by the electrical heating unit.

14. The method of claim 13, further comprising the step for securing the electrical heating unit to the patient's skin.

15. The method of claim 10, wherein the receiving surface comprises one of:
 (i) a rate limiting membrane and pharmaceutical formulation disposed in the dermal drug delivery system;
 (ii) healing skin of the patient; and
 (iii) a storage site located under a layer of skin.

16. The method of claim 10, further comprises the step for selectively passing the heat to facilitate transdermal absorption of a pharmaceutical formulation into the patient.

17. The method of claim 16, wherein the step for selectively passing further comprises the step for passing the heat to increase a solubility of an active ingredient in a pharmaceutical formulation dispersed within the dermal drug delivery system into the patient.

18. The method of claim 10, further comprising the step for maintaining a temperature range at the receiving surface below 60° centigrade.

19. An electrical heating apparatus kit configured to selectively heat a patient's skin in an area associated with a dermal drug delivery system, the kit comprising:
 a dermal drug delivery system configured to selectively deliver a predetermined amount of a pharmaceutical formulation to a patient; and
 an electrical heat generating unit having a feedback mechanism to selectively provide an amount of heat to at least one of:
 (i) the dermal drug delivery system; and
 (ii) the area of the patient's skin associated with the dermal drug delivery system.

20. The electrical heating apparatus kit of claim 19, further comprising a temperature sensor configured to selectively monitor the amount of heat provided.

\* \* \* \* \*